US011795201B2

(12) United States Patent
Wang et al.

(10) Patent No.: US 11,795,201 B2
(45) Date of Patent: Oct. 24, 2023

(54) BROWN FAT-SELECTIVE ADIPOKINES

(71) Applicant: UNIVERSITY OF MASSACHUSETTS, Boston, MA (US)

(72) Inventors: Yong-Xu Wang, Southborough, MA (US); Qingbo Chen, Worcester, MA (US)

(73) Assignee: University of Massachusetts, Boston, MA (US)

(*) Notice: Subject to any disclaimer, the term of this patent is extended or adjusted under 35 U.S.C. 154(b) by 552 days.

(21) Appl. No.: 16/604,692

(22) PCT Filed: Apr. 13, 2018

(86) PCT No.: PCT/US2018/027463
§ 371 (c)(1),
(2) Date: Oct. 11, 2019

(87) PCT Pub. No.: WO2018/191599
PCT Pub. Date: Oct. 18, 2018

(65) Prior Publication Data
US 2020/0377565 A1 Dec. 3, 2020

Related U.S. Application Data

(60) Provisional application No. 62/485,715, filed on Apr. 14, 2017.

(51) Int. Cl.
| | |
|---|---|
| *C07K 14/47* | (2006.01) |
| *A61P 3/10* | (2006.01) |
| *A61K 35/76* | (2015.01) |
| *C12N 15/62* | (2006.01) |
| *C12N 15/86* | (2006.01) |
| *A61K 38/00* | (2006.01) |
| *A61K 38/17* | (2006.01) |
| *C12N 15/00* | (2006.01) |
| *C12N 15/861* | (2006.01) |

(52) U.S. Cl.
CPC .......... *C07K 14/4705* (2013.01); *A61K 35/76* (2013.01); *A61P 3/10* (2018.01); *C12N 15/62* (2013.01); *C12N 15/86* (2013.01); *A61K 38/00* (2013.01); *A61K 38/17* (2013.01); *C07K 2319/00* (2013.01); *C12N 15/00* (2013.01); *C12N 15/861* (2013.01); *C12N 2750/14143* (2013.01)

(58) Field of Classification Search
CPC ... C07K 14/4705; C07K 2319/00; A61P 3/10; A61K 35/76; A61K 38/00; A61K 38/17; C12N 15/62; C12N 15/86; C12N 15/00; C12N 15/861; C12N 2750/14143
See application file for complete search history.

(56) References Cited

U.S. PATENT DOCUMENTS

2009/0239796 A1   9/2009   Fineman et al.

FOREIGN PATENT DOCUMENTS

| WO | 2001064834 A2 | 9/2001 |
|---|---|---|
| WO | WO 2005/016962 | 2/2005 |

OTHER PUBLICATIONS

Health Risks Linked to Obesity, from https://www.webmd.com/diet/obesity/obesity-health-risks, Sep. 15, 2020, pp. 1-3.*
Obesity Prevention Source, from https://www.hsph.harvard.edu/obesity-prevention-source/obesity-consequences/health-effe . . . , pp. 1-15, accessed Apr. 13, 2022.*
Drumm etal, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Hu et al. "Preclinical Dose-Finding Study With a Liver-Tropic, Recombinant AAV-2/8 Vector in the Mouse Model of Galactosialidosis," Molecular Therapy, Feb. 1, 2012 (Feb. 1, 2012), vol. 20, No. 2, pp. 267-274. entire document.
Delgado et al. "Diabetes Associated Genes from the Dark Matter of the Human Proteome," MOJ Proteomics & Bioinformatics, Jul. 19, 2014 (Jul. 19, 2014), vol. 1, No. 4, pp. 1-8. entire document.
Fox et al. "Genome-Wide Association for Abdominal Subcutaneous and Visceral Adipose Reveals a Novel Locus for Visceral Fat in Women," PLoS Genet, May 10, 2012 (May 10, 2012), vol. 8, Iss. 5, e1002695, pp. 1-14. entire document.
PCT International Search Report and Written Opinion in International Appln. No. PCT/US2018/027463, dated Jul. 24, 2018, 14 pages.
Badman et al., "Hepatic fibroblast growth, factor 21 is regulated by PPARα and is a key mediator of hepatic lipid metabolism in ketotic states," Cell Metabolism, Jun. 6, 2007, 5(6):426-37.
Boström et al., "A PGC1-α-dependent myokine that drives brown-fat-like development of white fat and thermogenesis," Nature, Jan. 2012, 481(7382):463-8.
Cohen et al., "Ablation of PRDM16 and beige adipose causes metabolic dysfunction and a subcutaneous to visceral fat switch," Cell, Jan. 16, 2014, 156(1-2):304-16.
Cristancho et al., "Forming functional fat: a growing understanding of adipocyte differentiation," Nature Reviews Molecular Cell Biology, Nov. 2011, 12(11):722-34.
Cypess et al., "Anatomical localization, gene expression profiling and functional characterization of adult human neck brown fat," Nature Medicine, May 2013, 19(5):635-9.
Cypess et al., "Identification and importance of brown adipose tissue in adult humans," New England Journal of Medicine, Apr. 9, 2009, 360(15):1509-17.
DeFronzo et al., "Pathogenesis of NIDDM: abalanced overview," Diabetes Care, Mar. 1, 1992, 15(3):318-68.

(Continued)

*Primary Examiner* — Li N Komatsu
(74) *Attorney, Agent, or Firm* — Fish & Richardson P.C.

(57) ABSTRACT

Methods of treating or reducing the risk of obesity and/or obesity-related disorders, e.g., metabolic syndrome, hepatic and non-hepatic steatosis, and diabetes, using C20orf27 proteins or nucleic acids.

8 Claims, 16 Drawing Sheets

Specification includes a Sequence Listing.

(56) References Cited

OTHER PUBLICATIONS

Farmer et al., "Molecular determinants of brown adipocyte formation and function," Genes & Development, May 15, 2008, 22(10):1269-75.
Farmer, "Transcriptional control of adipocyte formation," Cell Metabolism, Oct. 1, 2006, 4(4):263-73.
Harms et al., "Brown and beige fat: development, function and therapeutic potential," Nature Medicine, Oct. 2013, 19(10):1252-63.
Inagaki et al., "Endocrine regulation of the fasting response by PPARα-mediated induction of fibroblast growth factor 21," Cell Metabolism, Jun. 6, 2007, 5(6):415-25.
Jespersen et al., "A classical brown adipose tissue mRNA signature partly overlaps with brite in the supraclavicular region of adult humans," Cell Metabolism, May 7, 2013, 17(5):798-805.
Kajimura et al., "Transcriptional control of brown fat development," Cell Metabolism, Apr. 7, 2010, 11(4):257-62.
Kharitonenkov et al., "FGF-21 as a novel metabolic regulator. The Journal of clinical investigation," Jun. 1, 2005, 115(6):1627-35.
Lidell et al., "Evidence for two types of brown adipose tissue in humans," Nature Medicine, May 2013, 19(5):631-4.
Martin et al., "Role of glucose and insulin resistance in development of type 2 diabetes mellitus: results of a 25-year follow-up study," The Lancet, Oct. 17, 1992, 340(8825):925-9.
Nedergaard et al., "Unexpected evidence for active brown adipose tissue in adult humans," American Journal of Physiology-Endocrinology and Metabolism, Aug. 2007, 293(2):E444-52.
Pan et al., "Twist-1 is a PPARδ-inducible, negative-feedback regulator of PGC-1α in brown fat metabolism," Cell, Apr. 3, 2009, 137(1):73-86.
PCT International Preliminary Report on Patentability in International Appln. No. PCT/US2018/027463, dated Oct. 15, 2019, 9 pages.
Puigserver et al., "A cold-inducible coactivator of nuclear receptors linked to adaptive thermogenesis," Cell, Mar. 20, 1998, 92(6):829-39.
Rosen et al., "Adipocyte differentiation from the inside out," Nature Reviews Molecular cell biology, Dec. 2006, 7(12):885-96.
Rosen et al., "What we talk about when we talk about fat," Cell, Jan. 16, 2014, 156(1-2):20-44.
Saito et al., "High incidence of metabolically active brown adipose tissue in healthy adult humans: effects of cold exposure and adiposity," Diabetes, Jul. 1, 2009, 58(7):1526-31.
Seale et al., "Transcriptional control of brown fat determination by PRDM16," Cell Metabolism, Jul. 11, 2007, 6(1):38-54.
Stanford el al., "A novel role for subcutaneous adipose tissue in exercise-induced improvements in glucose homeostasis," Diabetes, Jun. 1, 2015, 64(6):2002-14.
Tontonoz et al., "Fat and beyond: the diverse biology of PPARγ," Annual Review of Biochemistry, Jul. 7, 2008, 77:289-312.
Uldry et al., "Complementary action of the PGC-1 coactivators in mitochondrial biogenesis and brown fat differentiation," Cell Metabolism, May 1, 2006, 3(5):333-41.
Van Marken Lichtenbelt et al., "Cold-activated brown adipose tissue in healthy men," New England Journal of Medicine, Apr. 9, 2009, 360(15):1500-8.
Virtanen et al., "Functional brown adipose tissue in healthy adults," New England Journal of Medicine, Apr. 9, 2009, 360(15):1518-25.
Wang et al., "The brown fat-enriched secreted factor Nrg4 preserves metabolic homeostasis through attenuation of hepatic lipogenesis," Nature Medicine, Dec. 2014, 20(12):1436.
Weyer et al., "The natural history of insulin secretory dysfunction and insulin resistance in the pathogenesis of type 2 diabetes mellitus," The Journal of Clinical Investigation, Sep. 15, 1999, 104(6):787-94.
Wu et al., "Beige adipocytes are a distinct type of thermogenic fat cell in mouse and human," Cell, Jul. 20, 2012, 150(2):366-76.
Zingaretti et al., "The presence of UCP1 demonstrates that metabolically active adipose tissue in the neck of adult humans truly represents brown adipose tissue," The FASEB Journal, Sep. 2009, 23(9):3113-20.
EP European Search Report in European Appln. No. 18785208.2, dated Feb. 19, 2021, 10 pages.
EP Office Action in European Appln. No. 18785208.2, dated Jan. 24, 2022, 5 pages.

\* cited by examiner

```
Mouse    1  MAAANRGSKPRVRSIRFAAGHDAEGSQSHVHFDEKLHDSVVMVTQESDNSFLVKVGFLKI
Human    2  MAAANKGNKPRVRSIRFAAGHDAEGSHSHVHFDEKLHDSVVMVTQESDSSFLVKVGFLKI
Identity ***** * ****************** ***************** *************

61  LHRYEITFTLPPVRRLSKDIRETPVHSLHLKLLSVTPTSEGYSIKCEYSAHKEGVLKEEM
        61  LHRYEITFTLPPVHRLSKDVREAPVPSLHLKLLSVVPEGYSVKCEYSAHKEGVLKEEI
            ************ ****** ** ** ******** * *** ************** *

121  LLACEGDIGTCVRVTVQARVMDRHHGTPMLLDGVKCVGAELEYDSEQSDWLGFD  174
       121  LLACEGGTGTCVRVTVQARVMDRHHGTPMLLDGVKCVGAELEYDSEHSDWHGFD  174
            ****** ************************************** *** ***
```

FIG. 2

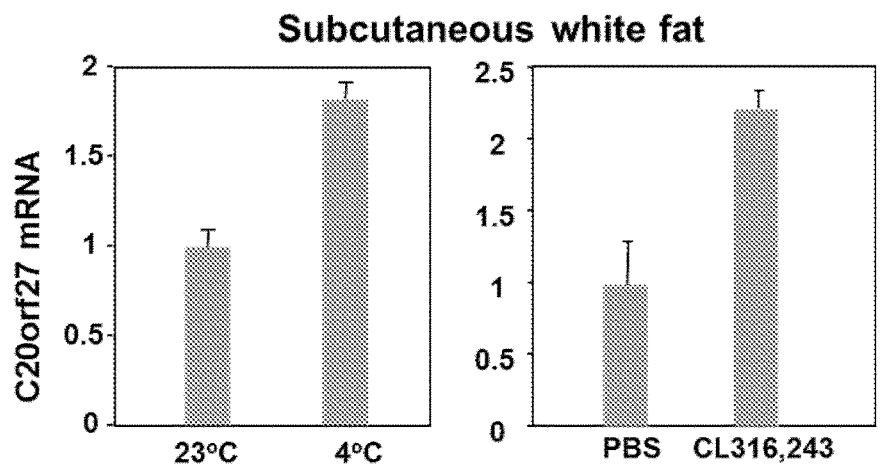
FIG. 4A
FIG. 4B
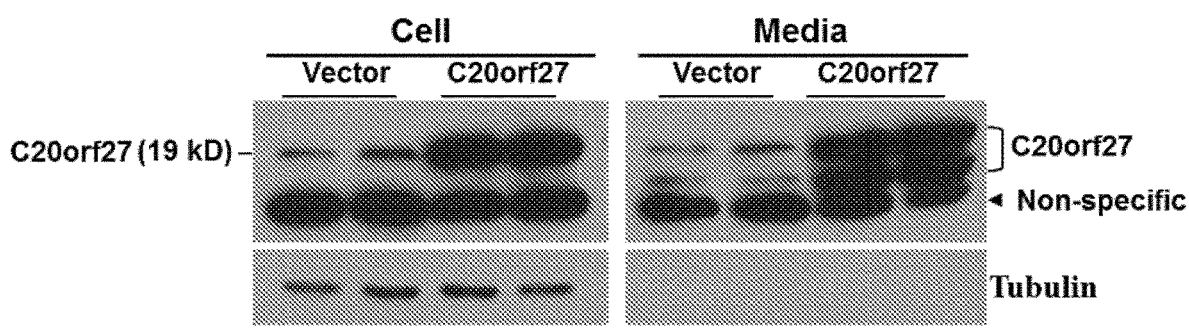
FIG. 5A
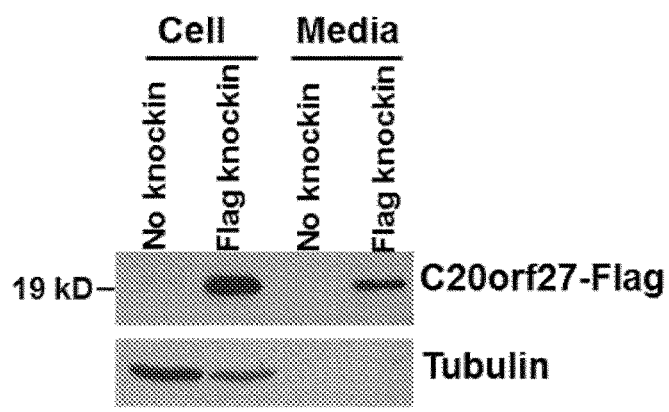
FIG. 5B

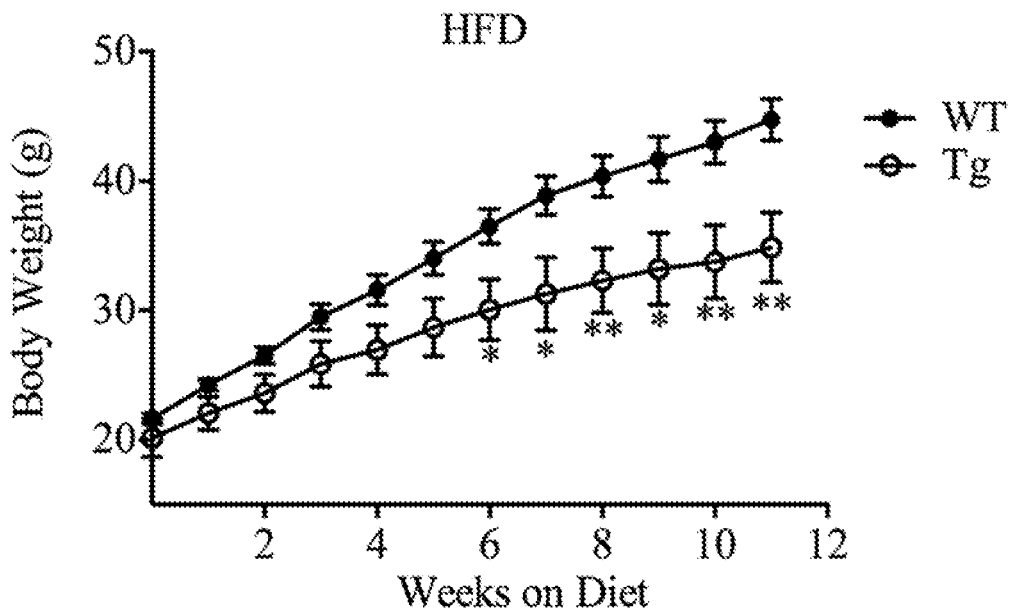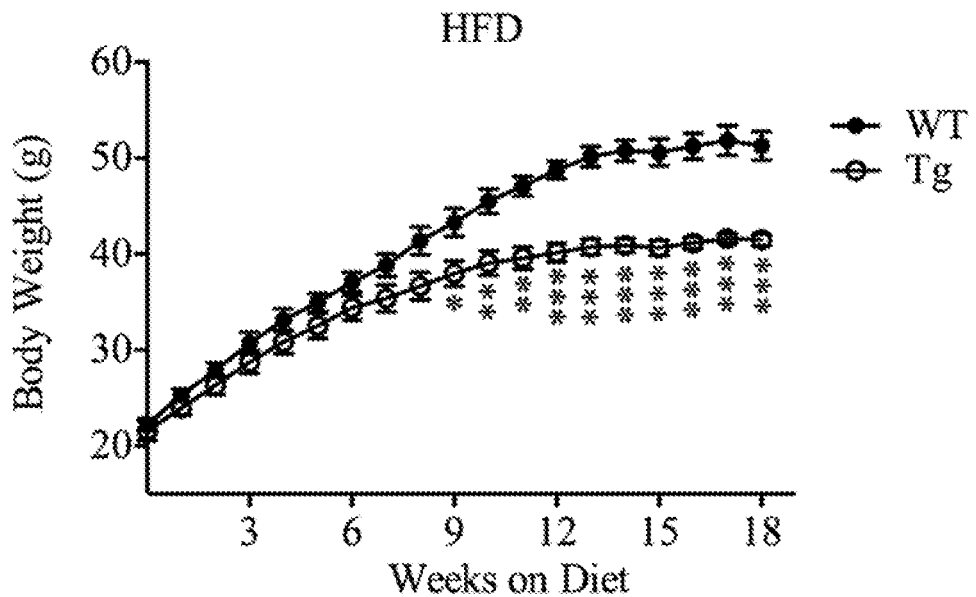
FIG. 8E

SEQUENCE LISTING

<160> NUMBER OF SEQ ID NOS: 9

<210> SEQ ID NO 1
<211> LENGTH: 199
<212> TYPE: PRT
<213> ORGANISM: Homo sapiens

<400> SEQUENCE: 1

```
Met Ala Ala Ala Asn Lys Gly Lys Cys Leu Pro Gly Val Val Gly Leu
1               5                   10                  15

Ala Gln Ala Leu Pro Val Gly Pro Gly Arg Arg Ala Ile Ala Ala Gly
                20                  25                  30

Asn Lys Pro Arg Val Arg Ser Ile Arg Phe Ala Ala Gly His Asp Ala
            35                  40                  45

Glu Gly Ser His Ser His Val His Phe Asp Glu Lys Leu His Asp Ser
        50                  55                  60

Val Val Met Val Thr Gln Glu Ser Asp Ser Ser Phe Leu Val Lys Val
65                  70                  75                  80

Gly Phe Leu Lys Ile Leu His Arg Tyr Glu Ile Thr Phe Thr Leu Pro
                85                  90                  95

Pro Val His Arg Leu Ser Lys Asp Val Arg Glu Ala Pro Val Pro Ser
            100                 105                 110

Leu His Leu Lys Leu Leu Ser Val Val Pro Val Pro Glu Gly Tyr Ser
        115                 120                 125

Val Lys Cys Glu Tyr Ser Ala His Lys Glu Gly Val Leu Lys Glu Glu
    130                 135                 140

Ile Leu Leu Ala Cys Glu Gly Gly Thr Gly Thr Cys Val Arg Val Thr
145                 150                 155                 160

Val Gln Ala Arg Val Met Asp Arg His His Gly Thr Pro Met Leu Leu
                165                 170                 175

Asp Gly Val Lys Cys Val Gly Ala Glu Leu Glu Tyr Asp Ser Glu His
            180                 185                 190

Ser Asp Trp His Gly Phe Asp
        195
```

<210> SEQ ID NO 2
<211> LENGTH: 174
<212> TYPE: PRT

<213> ORGANISM: Homo sapiens

<400> SEQUENCE: 2

Met Ala Ala Ala Asn Lys Gly Asn Lys Pro Arg Val Arg Ser Ile Arg
1               5                   10                  15

Phe Ala Ala Gly His Asp Ala Glu Gly Ser His Ser Val His Phe
            20                  25                  30

Asp Glu Lys Leu His Asp Ser Val Val Met Val Thr Gln Glu Ser Asp
            35                  40                  45

Ser Ser Phe Leu Val Lys Val Gly Phe Leu Lys Ile Leu His Arg Tyr
        50                  55                  60

Glu Ile Thr Phe Thr Leu Pro Pro Val His Arg Leu Ser Lys Asp Val
65                  70                  75                  80

Arg Glu Ala Pro Val Pro Ser Leu His Leu Lys Leu Leu Ser Val Val
                85                  90                  95

Pro Val Pro Glu Gly Tyr Ser Val Lys Cys Glu Tyr Ser Ala His Lys
                100                 105                 110

Glu Gly Val Leu Lys Glu Glu Ile Leu Ala Cys Glu Gly Gly Thr
            115                 120                 125

Gly Thr Cys Val Arg Val Thr Val Gln Ala Arg Val Met Asp Arg His
    130                 135                 140

His Gly Thr Pro Met Leu Leu Asp Gly Val Lys Cys Val Gly Ala Glu
145                 150                 155                 160

Leu Glu Tyr Asp Ser Glu His Ser Asp Trp His Gly Phe Asp
                165                 170

<210> SEQ ID NO 3
<211> LENGTH: 174
<212> TYPE: PRT
<213> ORGANISM: Mus musculus

<400> SEQUENCE: 3

Met Ala Ala Ala Asn Arg Gly Ser Lys Pro Arg Val Arg Ser Ile Arg
1               5                   10                  15

Phe Ala Ala Gly His Asp Ala Glu Gly Ser Gln Ser Val His Phe
            20                  25                  30

Asp Glu Lys Leu His Asp Ser Val Val Met Val Thr Gln Glu Ser Asp
            35                  40                  45

Asn Ser Phe Leu Val Lys Val Gly Phe Leu Lys Ile Leu His Arg Tyr
        50                  55                  60

Glu Ile Thr Phe Thr Leu Pro Pro Val Arg Arg Leu Ser Lys Asp Ile
65                  70                  75                  80

Arg Glu Thr Pro Val His Ser Leu His Leu Lys Leu Leu Ser Val Thr
                85                  90                  95

Pro Thr Ser Glu Gly Tyr Ser Ile Lys Cys Glu Tyr Ser Ala His Lys
                100                 105                 110

Glu Gly Val Leu Lys Glu Glu Met Leu Leu Ala Cys Glu Gly Asp Ile
            115                 120                 125

Gly Thr Cys Val Arg Val Thr Val Gln Ala Arg Val Met Asp Arg His
    130                 135                 140

His Gly Thr Pro Met Leu Leu Asp Gly Val Lys Cys Val Gly Ala Glu
145                 150                 155                 160

Leu Glu Tyr Asp Ser Glu Gln Ser Asp Trp Leu Gly Phe Asp
                165                 170

```
<210> SEQ ID NO 4
<211> LENGTH: 19
<212> TYPE: PRT
<213> ORGANISM: Artificial
<220> FEATURE:
<223> OTHER INFORMATION: peptide fragment identified in C20orf27

<400> SEQUENCE: 4

Phe Ala Ala Gly His Asp Ala Glu Gly Ser Gln Ser His Val His Phe
1               5                   10                  15

Asp Glu Lys

<210> SEQ ID NO 5
<211> LENGTH: 11
<212> TYPE: PRT
<213> ORGANISM: Artificial
<220> FEATURE:
<223> OTHER INFORMATION: peptide fragment identified in C20orf27

<400> SEQUENCE: 5

Tyr Glu Ile Thr Phe Thr Leu Pro Pro Val Arg
1               5                   10

<210> SEQ ID NO 6
<211> LENGTH: 10
<212> TYPE: PRT
<213> ORGANISM: Artificial
<220> FEATURE:
<223> OTHER INFORMATION: peptide fragment identified in C20orf27

<400> SEQUENCE: 6

Glu Thr Pro Val His Ser Leu His Leu Lys
1               5                   10

<210> SEQ ID NO 7
<211> LENGTH: 14
<212> TYPE: PRT
<213> ORGANISM: Artificial
<220> FEATURE:
<223> OTHER INFORMATION: peptide fragment identified in C20orf27

<400> SEQUENCE: 7

Leu Leu Ser Val Thr Pro Thr Ser Glu Gly Tyr Ser Ile Lys
1               5                   10

<210> SEQ ID NO 8
<211> LENGTH: 12
<212> TYPE: PRT
<213> ORGANISM: Artificial
<220> FEATURE:
<223> OTHER INFORMATION: peptide fragment identified in C20orf27

<400> SEQUENCE: 8

His His Gly Thr Pro Met Leu Leu Asp Gly Val Lys
1               5                   10

<210> SEQ ID NO 9
<211> LENGTH: 19
<212> TYPE: DNA
<213> ORGANISM: Artificial
<220> FEATURE:
<223> OTHER INFORMATION: lentiviral shRNA

<400> SEQUENCE: 9
gacaacagct tcttagtca                                                19
```

BROWN FAT-SELECTIVE ADIPOKINES

CLAIM OF PRIORITY

This application is a U.S. National Stage Application under 35 USC § 371 of International Patent Application Serial No. PCT/US2018/027463 filed on Apr. 13, 2018, entitled "Brown Fat-Selective Adipokines," which claims the benefit of U.S. Provisional Patent Application Ser. No. 62/485,715, filed on Apr. 14, 2017. The entire contents of the foregoing are hereby incorporated by reference.

STATEMENT OF FEDERALLY SPONSORED RESEARCH

This invention was made with Government support under Grant Numbers DK076118 and DK098594 awarded by the National Institutes of Health. The Government has certain rights in the invention.

TECHNICAL FIELD

This invention relates to methods of treating obesity, metabolic syndrome, hepatic and non-hepatic steatosis, and diabetes using C20orf27 proteins or nucleic acids.

BACKGROUND

Obesity is caused by a long-term imbalance between energy intake and energy expenditure, and is a strong risk factor for a myriad of metabolic diseases, including insulin resistance and type 2 diabetes. Adipose tissues serve as major sites to control energy balance[1]. They are present in two functionally distinct types, brown fat and white fat. Brown fat is specialized for energy expenditure by dissipating energy as heat in a process called nonshivering thermogenesis that is critically dependent on the expression of mitochondrial inner membrane protein Ucp1. By contrast, the primary function of white fat is to store excess energy in the form of triglycerides. However, not all white fat depots are created equal. For example, visceral fat depot and subcutaneous fat depot each possesses unique gene expression signature, and visceral fat depot is associated with insulin resistance, diabetes, hyperlipidemia, and hepatic steatosis, while subcutaneous fat depot is considered relatively benign. Moreover, subcutaneous fat displays considerable plasticity and can be converted into brown-like (also named as beige or brite) adipocytes at proper conditions. Brown and brown-like adipocytes not only promote energy expenditure, but also improve glycemic conditions independently of changes of body weight (see, e.g., Stanford et al., Diabetes 64, 2002-2014 (2015); Cohen et al., Cell 156, 304-316 (2014)).

Studies in recent years have demonstrated that adult humans possess both classical brown fat depots and beige adipocytes, and their activities are inversely associated with human obesity[2-11], raising the idea that increasing brown fat mass/activity, promoting browning of white fat, or switching visceral fat to subcutaneous fat might hold promise for the treatment of obesity and associated metabolic diseases.

SUMMARY

Adult humans possess both brown fat depots and beige adipocytes and their activities are inversely associated with human obesity. Increasing brown fat mass/activity or promoting browning of white fat has been considered a strategy for treatment of obesity and type 2 diabetes, and their associated metabolic diseases. To date, many of the identified genes important for brown and beige adipocyte development are not ideal therapeutic targets, thus novel druggable targets without side effects are urgently need in this space. Described herein is the identification of a previously uncharacterized, secreted protein that is exclusively expressed in the adipose tissue, in particular brown fat. This adipokine is highly conserved in mammals. In humans, it is encoded by open reading frame C20orf27, and its mouse ortholog is encoded by 1700037H04RIK. It is referred to herein as C20orf27. As shown herein, C20orf27 promotes the browning of white fat and lowers blood glucose level. Described herein are in vitro and in vivo experiments, including hepatic viral expression, and C20orf27 transgenic and knockout mice, that investigated the pharmacological and physiological roles of C20orf27 in brown and beige adipocyte specification, energy expenditure, obesity resistance and insulin sensitivity, and demonstrate that C20orf27 is useful as an anti-obesity and/or anti-diabetic biologic.

Thus, provided herein are methods for treating, or reducing risk of, obesity or a disorder associated with obesity, or improving glycemic control (in obese and non-obese diabetics and pre-diabetic subjects), in mammalian subjects, e.g., human or non-human (e.g., veterinary subjects including pets, livestock, and zoo animals). The methods include administering a therapeutically effective amount of Chromosome 20 Open Reading Frame 27 (C20orf27) to a subject in need thereof.

In some embodiments, the disorder associated with obesity is diabetes, metabolic syndrome, fatty liver disease, non-hepatic steatosis.

In some embodiments, the subject has a BMI of at least 25, or at least 30.

In some embodiments, wherein the subject is human.

In some embodiments, the methods include administering (i) a polypeptide comprising a sequence that is at least 80% identical to SEQ ID NO:2, or an active fragment thereof, or (ii) a nucleic acid encoding a polypeptide comprising a sequence that is at least 80% identical to SEQ ID NO:2, or an active fragment thereof.

In some embodiments, the methods include administering (i) a polypeptide comprising a sequence that is at least 95% identical to SEQ ID NO:2, or an active fragment thereof, or (ii) a nucleic acid encoding a polypeptide comprising a sequence that is at least 95% identical to SEQ ID NO:2, or an active fragment thereof.

In some embodiments, the nucleic acid is administered in a viral vector. In some embodiments, the viral vector is an adeno-associated viral (AAV) vector, e.g., an AAV selected from the group consisting of AAV8, AAV-2/8, AAV2 (Y→F), AAV7, AAV-HSC15, AAV-HSC17, AAV-HSC15/17, AAVhu.37 and AAVrh.8.

In some embodiments, the polypeptide is administered parenterally, e.g., intravenously, intramuscularly, or subcutaneously.

In some embodiments, the polypeptide comprises one or more modifications, e.g., one or more of: replacement of one or more L amino acids with D amino acids; acetylation (e.g., comprises an N-acetylalanine at position 2), amidation; conjugation to a linear or branched-chain monomethoxy poly-ethylene glycol (PEG, i.e., is PEGylation); modification of the N- or C-terminus; glycosylation; polysialic acid (PSA) addition to a glycan; or fusion to a non-C20orf27 protein, e.g., Fc fusion proteins, fusion to human serum albumin, fusion to transferrin, or fusion to carboxy-terminal peptide of chorionic gonadotropin (CG) β-chain.

Also provided herein are viral vectors comprising a nucleic acid encoding a polypeptide comprising a sequence that is at least 80% identical to SEQ ID NO:2, or an active fragment thereof. In some embodiments, the viral vector is an adeno-associated viral (AAV) vector, e.g., an AAV selected from the group consisting of AAV8, AAV-2/8, AAV2 (Y→F), AAV7, AAV-HSC15, AAV-HSC17, AAV-HSC15/17, AAVhu.37 and AAVrh.8.

In some embodiments, the viral vectors used in the methods and compositions herein include a promoter for expression of the polypeptide in liver or adipose cells. For example, for liver expression, a human thyroid hormone-binding globulin promoter or albumin promoter can be used. For adipose expression, an aP2 promoter or adiponectin promoter can be used.

Also provided herein are isolated polypeptides that are at least 80% identical to SEQ ID NO:2, or an active fragment thereof, and optionally comprise one or more modifications.

In some embodiments, the modification include one or more of: replacement of one or more L amino acids with D amino acids; acetylation (e.g., comprises an N-acetylalanine at position 2), amidation; conjugation to a linear or branched-chain monomethoxy poly-ethylene glycol (PEG); modification of the N- or C-terminus; glycosylation; poly-sialic acid (PSA) addition to a glycan; or fusion to a non-C20orf27 protein, e.g., Fc fusion proteins, fusion to human serum albumin, fusion to transferrin, or fusion to carboxy-terminal peptide of chorionic gonadotropin (CG) β-chain.

Also provided herein are pharmaceutical compositions comprising the nucleic acids, viral vectors, and/or the isolated polypeptides described herein, and a pharmaceutically acceptable carrier, as well as the use thereof in methods of treating, or reducing risk of, obesity or a disorder associated with obesity in a mammalian subject.

In some embodiments, the disorder associated with obesity is diabetes, metabolic syndrome, fatty liver disease, non-hepatic steatosis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2. Amino acid sequence alignment of mouse (SEQ ID NO:3) and human (SEQ ID NO:2) C20orf27 with identical residues marked by an asterisk. Five unique peptides identified by Mass Spectrometry analysis of conditional media collected from brown adipocyte culture are underlined with dots or dashes. The asterisks underneath indicate identity between the two species.

FIG. 4A. C20orf27 mRNA levels in mice (n=4/group) that were cold challenged for 6 hr at 4° C. or left at room temperature.

FIG. 4B. C20orf27 mRNA levels in mice (n=4/group) that were given a single dose of i.p. injection of β3-adrenergic receptor agonist CL316,243. Tissues were harvested 24 hr post injection.

FIG. 5A. Detection of C20orf27 protein in intracellular and medium fraction of brown adipocytes infected with adenovirus expressing vector (control) or C20orf27.

FIG. 5B. Detection of C20orf27 protein using anti-FLAG antibody in intracellular and medium fraction of brown adipocytes containing a Flag tag knockin at the C-terminus of genomic locus of C20orf27.

FIGS. 8A-8F. Transgenic C20orf27 fat-specific animals expressed higher levels of UCP1 and mitochondrial enzymes in white adipocytes (8A), were more cold-tolerant (8B) and had improved glucose tolerance compared with wild type littermates (8C). Serum from C20orf27 transgenic mice induced Ucp1 expression in cultured white fat adipocytes (8D). In addition, the C20orf27 transgenic mice gained less body weight on a high fat diet (8E, two separate cohorts) and had less liver lipid accumulation (8F).

DETAILED DESCRIPTION

Figure 1:
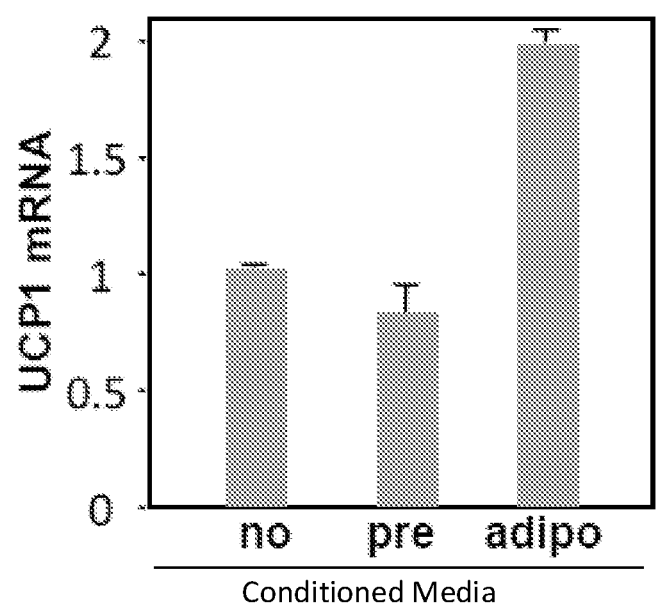
FIG. 1. Conditioned media collected from immortalized brown preadipocytes (pre) and mature adipocytes (adipo) was added to primary white adipocyte culture. Ucp1 expression was examined.

The success of utilization of brown or beige adipocytes as therapeutic targets depends on a complete understanding of the molecular mechanisms underlying brown fat development. This area of research has been extensively studied at the transcriptional level. In brief, terminal differentiation of brown adipocytes ultimately requires simultaneous execution of two intertwined transcriptional programs. One is the Pparg-controlled program that was initially elucidated from studies of white adipocyte differentiation[12-15]. Pparg drives the expression of adipocyte genes that are common to both white and brown fat, and is essential for adipogenesis of both fat types. The second program is the expression of brown fat-selective genes including Ucp1, which is primarily controlled by brown fat-enriched transcriptional co-activators Prdm16 and Pgc-1a and Pgc-1b[12, 16-20]; interestingly, none of these co-activators is required for adipogenesis per se[19,21]. Recent studies have also discovered several transcriptional components that are capable of directing both programs[16]. To date, however, the therapeutic potential remains elusive for all the identified key brown fat transcriptional regulators, due to the fact that they are not ideal druggable candidates.

Initially considered an inert compartment, adipose tissue has now been appreciated as a secretory organ. Notable examples of secreted proteins include leptin, resistin, adiponectin, and adipsin, which, by exerting on other tissues, have profound effects on energy intake, insulin sensitivity, and insulin secretion. Interestingly, leptin and resistin are exclusively expressed in white fat, whereas adiponectin and adipsin are produced by both white fat and brown fat. More recently, Neuregulin 4, a member of the epidermal growth factor family of extracellular ligands, was found to be produced by brown fat and regulate neurite outgrowth and hepatic steatosis[22]. Although factors secreted by skeletal and liver, such as Irisin[23] and Fgf21[24-26] respectively, have been shown to promote browning of white fat, until now, brown fat-selective secreted proteins important for brown fat development or browning of white fat have not been described. Described herein is a previously uncharacterized, brown fat-secreted protein, referred to herein as C20orf27, that plays a critical role in brown fat determination and beige adipocyte formation, and its use in treating obesity and type 2 diabetes.

Through both Western blot analysis and mass spectrometry, the present inventors demonstrated that C20orf27 gene product is a brown fat-secreted protein. When C20orf27 is adenovirally expressed in either brown and white adipocytes in vitro, UCP1 expression is markedly induced. Treatment of white adipocytes with condition medium form C20orf27-overexpressing HEK293 cells increases UCP1 expression. The present inventors generated transgenic mice expressing C20orf27 in adipose tissue, and found that Ucp1 and mitochondrial genes are highly induced in the white fat of the transgenic mice. Importantly, the browning of white fat in the transgenic mice protects against high fat diet-induced obesity, liver steatosis and glucose intolerance. When serum was collected from the C20orf27 transgenic mice and used to treat cultured white adipocytes, Ucp1 was induced compared with serum from control mice, demonstrating that circulating C20orf27 is functional. The present inventors infused C20orf27 expressing adenovirus into liver of wild type mice. One week after infusion, Ucp1 was induced in the white fat and blood glucose level is lowered compared with GFP adenovirus infusion. Thus, C20orf27 protein produced in the liver appears to travel to the white fat through circulation to induce Ucp1 expression.

In conclusion, the C20orf27 gene product is a bone fide adipokine, and exogenous delivery of this adipokine or its chemical mimics into humans has the potential to convert white fat to brown-like fat, elevate energy expenditure, ameliorate obesity and fatty liver, and improve glucose homeostasis.

Chromosome 20 Open Reading Frame 27 (C20orf27)

C20orf27 is a previously uncharacterized polypeptide that is exclusively expressed in the adipose tissue with a significant and high enrichment in brown fat versus white fat. The polypeptide is encoded by open reading frame C20orf27 in human, which has two isoforms. Isoform 2 is a 19 Kd protein with 174 amino acids, and shares 90% identity between mouse and human (FIG. 2). Exemplary sequences of human C20orf27 are shown in Table 1.

TABLE 1

Exemplary human C20orf27 sequences

| Variant | NCBI RefSeq ID | Isoform | NCBI RefSeq ID |
| --- | --- | --- | --- |
| 1 | NM_001039140.2 | 1 | NP_001034229.1 |
| 2 | NM_001258429.1 | 2 | NP_001245358.1 |
| 3 | NM_001258430.1 | 2 | NP_001245359.1 |

Variant 1 encodes the longer isoform 1. Variant 2 uses an alternate splice site in the coding region, and variant 3 differs in the 5' UTR and uses an alternate splice site in the coding region, but variants 2 and 3 maintain the same reading frame as variant 1. Variants 2 and 3 encode the same isoform 2, which is shorter than isoform 1.

Exemplary protein sequences for isoforms 1 and 2 are shown below. As shown in uppercase letters, isoform 1 has a 25-amino acid extension at the N-terminus compared with isoform 2.

```
NP_001034229.1 UPF0687 protein C20orf27 isoform 1
                                         (SEQ ID NO: 1)
   1 MAAANKGKCL PGVVGLAQAL PVGPGrraia agnkprvrsi
rfaaghdaeg shshvhfdek
  61 lhdsvvmvtq esdssflvkv gflkilhrye itftlppvhr
lskdvreapv pslhlkllsv
 121 vpvpegysvk ceysahkegv lkeeillace ggtgtcvrvt
vqarvmdrhh gtpmlldgvk
 181 cvgaeleyds ehsdwhgfd
```

```
NP_001245358.1 UPF0687 protein C20orf27 isoform 2
                                         (SEQ ID NO: 2)
   1 maaankgnkp rvrsirfaag hdaegshshv hfdeklhdsv
vmvtqesdss flvkvgflki
  61 lhryeitftl ppvhrlskdv reapvpslhl kllsvvpvpe
gysvkceysa hkegvlkeei
 121 llaceggtgt cvrvtvqary mdrhhgtpml ldgvkcvgae
leydsehsdw hgfd
```

In some embodiments, isoform 2 or an active fragment thereof is used. In some embodiments, isoform 1 or an active fragment thereof is used. Active fragments are those that induce the expression of Ucp1 in cultured white adipose cells. In some embodiments, the active fragment includes the "Domain of unknown function (DUF4517);

pfam15006," i.e., amino acids 28-173 of isoform 2, or amino acids 53-198 of isoform 1. In some embodiments, isoform 2 is used.

Additional homologs of C20orf27 are provided in Table 2.

TABLE 2

Homologs of Human C20orf27

| Homolog, species<br>Full name | GenBank Acc. No.<br>Length in aa |
|---|---|
| C20orf27, H.sapiens<br>chromosome 20 open reading frame 27 | NP_001034229.1<br>199 aa |
| C20H20orf27, P.troglodytes<br>chromosome 20 open reading frame,<br>human C20orf27 | XP_530265.2<br>199 aa |
| C10H20orf27, M.mulatta<br>UPF0687 protein C20orf27-like | XP_001115327.1<br>199 aa |
| C24H20orf27, C.lupus<br>chromosome 24 open reading frame,<br>human C20orf27 | XP_005634887.1<br>190 aa |
| C13H20orf27, B.taurus<br>chromosome 13 open reading frame,<br>human C20orf27 | NP_001039670.1<br>174 aa |
| 1700037H04Rik, M.musculus<br>RIKEN cDNA 1700037H04 gene | NP_080367.1<br>174 aa |
| RGD1311739, R.norvegicus<br>similar to RIKEN cDNA 1700037H04 | NP_001020862.1<br>174 aa |
| LOC100858801, G.gallus<br>UPF0687 protein C20orf27 homolog | XP_003643512.2<br>380 aa |
| c20orf27, X.tropicalis<br>chromosome 20 open reading frame 27 | NP_001007504.1<br>174 aa |
| LOC560941, D.rerio<br>UPF0687 protein C20orf27 homolog | XP_689433.5<br>173 aa |

The C20orf27 compositions used in the methods described herein can include a peptide that is at least 80%, e.g., at least 85%, 90%, or 95% identical to the amino acid sequence of SEQ ID NO:1 or SEQ ID NO:2, e.g., have differences at up to 5%, 10%, 15%, or 20% of the residues of SEQ ID NO:1 or SEQ ID NO:2 replaced, e.g., with conservative mutations, or deleted. Alternatively, the compositions can include nucleic acids that encode peptide that is at least 80%, e.g., at least 85%, 90%, or 95% identical to the amino acid sequence of SEQ ID NO:1 or SEQ ID NO:2, e.g., have differences at up to 5%, 10%, 15%, or 20% of the residues of SEQ ID NO:1 or SEQ ID NO:2 replaced, e.g., with conservative mutations, or deleted. The variants useful in the present methods retain a desired activity of the parent, e.g., the ability to induce the expression of UCP1 or mitochondrial genes in cultured white or brown adipocytes, or to activate protein kinase A (PKA) in cultured white adipose cells, or to activate kinase Akt in liver cells.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. See, e.g., Altschul et al. (2005) FEBS J. 272:5101-5109. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blosum62 scoring matrix with a gap penalty of 11,1.

In some embodiments, the protein includes one or more modifications, e.g., is acetylated (e.g., comprises an N-acetylalanine at position 2), amidated, conjugation to either linear or branched-chain monomethoxy poly-ethylene glycol (PEG, i.e., PEGylation), modification of the N- or C-terminus, glycosylation, polysialic acid (PSA) addition to a glycan, or fusion proteins, e.g., Fc fusion proteins, fusion to human serum albumin, fusion to carboxy-terminal peptide, and other polypeptide fusion approaches to make drugs with more desirable pharmacokinetic profiles; see, e.g., Werle and Bernkop=Schnürch, Amino Acids. 2006 June; 30(4):351-67; Strohl, BioDrugs. 2015; 29(4): 215-239.

Methods of Treatment

The methods described herein include methods for the treatment of obesity and disorders associated with obesity, e.g., diabetes and metabolic syndrome. In some embodiments, the disorder is diet-induced obesity, e.g., high-calorie or high-fat diet induced obesity. Generally, the methods include administering a therapeutically effective amount of a C20orf27 peptide or nucleic acid encoding the C20orf27 peptide as described herein, to a subject who is in need of, or who has been determined to be in need of, such treatment.

As used in this context, to "treat" means to ameliorate at least one symptom of obesity or a disorder associated with obesity. Often, obesity results in hyperglycemia; thus, a treatment can result in a reduction in blood glucose levels and a return or approach to normoglycemia, and/or a reduction in BMI. Administration of a therapeutically effective amount of a compound described herein for the treatment of obesity will result in decreased body weight or fat.

Administration of a therapeutically effective amount of a compound described herein for the treatment of fatty liver disease (FLD) will result in, e.g., a decrease or stabilization of fat levels in the liver; a decrease or stabilization of inflammation levels in the liver; or a reduction, delay or prevention of development of NASH, fibrosis, cirrhosis, or liver failure. In some embodiments, administration of a therapeutically effective amount of a compound described herein for the treatment of FLD will result in decreased or no increase in intra-cytoplasmic accumulation of triglyceride (neutral fats), and an improvement or no decline in liver function.

Diabetic and Pre-Diabetic Subjects

In some embodiments, the subjects treated by the methods described herein have diabetes, i.e., are diabetic. A person who is diabetic has one or more of a Fasting Plasma Glucose Test result of 126 mg/dL or more; a 2-Hour Plasma Glucose Result in a Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and beta-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes. Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

As shown herein, C20orf27 can improve glucose homeostasis in both lean and obese mice. So C20orf27 can be used to improve glycemic control in diabetic patients (regardless of whether they are obese or not). This includes improving the maintenance of blood glucose levels within a desired range, e.g., maintaining a hemoglobin A1c (HbA1c) level below a desired range, e.g., below 7%.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
| --- | --- |
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |

| Oral Glucose Tolerance Test (OGTT) [except pregnancy] (2 hours after a 75-gram glucose drink) | |
| --- | --- |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in Table 3.

TABLE 3

| Category | BMI |
| --- | --- |
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Metabolic Syndrome

In some embodiments, the methods include determining whether a subject has the metabolic syndrome, and selecting the subject if they do have the metabolic syndrome, then administering an inhibitory nucleic acid as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes. 37(12):1595-1607 (1988)), refers to a clustering of obesity, dyslipidemia, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359

(2002)). Insulin resistance is now felt to be central in the pathogenesis of these related disorders.

Fatty Liver Disease (FLD)

Nonalcoholic fatty liver disease (NAFLD) and its most severe form, nonalcoholic steatohepatitis (NASH), are associated with high fat diet, high triglyceride levels, obesity, the metabolic syndrome and type II diabetes, and pose an increased risk of cardiovascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma. FLD can be caused by excessive alcohol consumption (alcoholic hepatitis), drugs (such as valproic acid and corticosteroids (e.g., cortisone or prednisone)), excessive Vitamin A, and obesity. A diagnosis of NAFLD or NASH can be made by methods known in the art, e.g., by histological examination of liver biopsy samples.

In some embodiments, the methods include determining whether a subject has FLD, and selecting the subject if they do have FLD, then administering a dose of a C20orf27 peptide or peptidomimetic as described herein. Determining whether a subject has FLD can include reviewing their medical history, or ordering or performing such tests as are necessary to establish a diagnosis.

Most individuals with FLD are asymptomatic; the condition is usually discovered incidentally as a result of abnormal liver function tests or hepatomegaly, e.g., noted in an unrelated medical condition. Elevated liver biochemistry is found in 50% of patients with simple steatosis (see, e.g., Sleisenger, Sleisenger and Fordtran's Gastrointestinal and Liver Disease. Philadelphia: W.B. Saunders Company (2006)). In general, the diagnosis begins with the presence of elevations in liver tests that are included in routine blood test panels, such as alanine aminotransferase (ALT) or aspartate aminotransferase (AST). Even modest, subclinical increases in hepatic fat accumulation have been shown to be an early component in the progressive pathogenesis of metabolic syndrome (see, e.g., Almeda-Valdés et al., Ann. Hepatol. 8 Suppl 1:S18-24 (2009); Polyzos et al., Curr Mol Med. 9(3):299-314 (2009); Byrne et al., Clin. Sci. (Lund). 116(7):539-64 (2009)).

Imaging studies are often obtained during evaluation process. Ultrasonography reveals a "bright" liver with increased echogenicity. Thus, medical imaging can aid in diagnosis of fatty liver; fatty livers have lower density than spleen on computed tomography (CT) and fat appears bright in T1-weighted magnetic resonance images (MRIs). Making a differential diagnosis of Nonalcoholic Steatohepatitis (NASH), as opposed to simple fatty liver, is done using a liver biopsy. For a liver biopsy, a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or Nonalcoholic Fatty Liver Disease (NAFLD) is diagnosed. Thus, histological diagnosis by liver biopsy is sought when assessment of severity is indicated.

Non-Hepatic Steatosis

Although the liver is most often associated with steatosis, it can occur in any organ, including but not limited to kidneys (renal steatosis, see, e.g., Bobulescu et al., Am J Physiol Renal Physiol. 2008 June; 294(6):F1315-22), heart (cardiac steatosis, see, e.g., McGavock et al., Circulation. 2007 Sep. 4; 116(10):1170-5; McGavock et al., Ann Intern Med. 2006 Apr. 4; 144(7):517-24), skeletal muscle, and vasculature (e.g., atherosclerosis); thus, the present methods may also be used to treat those conditions. See, e.g., Federico et al., World J Gastroenterol. 2010 Oct. 14; 16(38): 4762-72.

Gene Therapy

The nucleic acids described herein, e.g., nucleic acids encoding an C20orf27 polypeptide or active fragment thereof, can be incorporated into a gene construct to be used as a part of a gene therapy protocol. Provided herein are expression vectors for in vivo transfection and expression of a polynucleotide that encodes a C20orf27 polypeptide or active fragment thereof, as described herein, e.g., in particular cell types, especially hepatic or adipose cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci.

USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). In some embodiments, a liver-tropic AAV is used, e.g., AAV8, AAV-2/8, AAV2 (Y→F), AAV7, AAV-HSC15, AAV-HSC17, AAV-HSC15/17, AAVhu.37 and AAVrh.8. See, e.g., Hu et al., Mol Ther. 2012 February; 20(2): 267-274; Asokan et al., Molecular Therapy 20(4): 699-708 (2012).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

The gene delivery system can include one or more regulatory sequences operatively linked to the C20orf27 nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. In some embodiments, the viral vectors used in the methods and compositions herein include a promoter for expression of the polypeptide in liver or adipose cells. For example, for liver expression, a human thyroid hormone-binding globulin promoter (see, e.g., Il, C. R. et al. Optimization of the human factor VIII complementary DNA expression plasmid for gene therapy of hemophilia A. Blood coagulation & fibrinolysis: an international journal in haemostasis and thrombosis 8 Suppl 2, S23-30 (1997)) or albumin promoter can be used. For adipose expression, an aP2 promoter (see, e.g., Ross, S. R. et al. A fat-specific enhancer is the primary determinant of gene expression for adipocyte P2 in vivo. Proceedings of the National Academy of Sciences of the United States of America 87, 9590-9594 (1990)) or adiponectin promoter (see, e.g., Eguchi, J. et al. Transcriptional control of adipose lipid handling by IRF4. Cell metabolism 13, 249-259 (2011)) can be used.

In addition to viral transfer methods, such as those illustrated above, non-viral methods can also be employed to cause expression of a nucleic acid compound described herein (e.g., a C20orf27 nucleic acid) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21):1867-74 (2000).

In some embodiments, a gene encoding C20orf27 as described herein is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include C20orf27 peptides described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of preferred routes of administration include parenteral, e.g., intravenous, intramuscular, or subcutaneous administration.

Methods of formulating suitable pharmaceutical compositions are known in the art, see, e.g., the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethyelene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the C20orf27 peptides are formulated with, e.g., liposomes or micelles. Biodegradable microparticle or nanoparticle delivery systems that increase intracellular uptake, e.g., polymeric and surface modified nanoparticles as described in US 2009/0136585, can also be used. Examples include poly DL-lactide-co-glycolide (PLGA) nanoparticles, e.g., surface-modified with known surface-modifying agents, such as heparin, dodecylmethyl-ammonium bromide (DMAB), DEAE-Dextran, lipofectin, and fibrinogen (see, e.g. Song et al., J. Control. Release, 54:201-211 (1998); Labhasetwar et al., J. Pharm. Sci., 87:1229-34 (1998); Lee et al., Biomaterials 29(9):1224-1232 (2008); and US 2009/0136585.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1. Brown Adipocyte-Secreted Factor(S) Promotes Browning of White Adipocytes Immortalized brown preadipocytes were differentiated into mature adipocytes as previously described[27], and conditional medium collected from the last 12 hours of differentiation. The medium was concentrated with a 3 kD cut-off concentrator, and added into primary subcutaneous inguinal white adipocytes during differentiation. As shown in FIG. 1, conditioned medium collected from mature brown adipocytes enhanced Ucp1 expression compared to conditional medium collected from brown preadipocytes or no conditional medium added, indicating the existence of secreted factor(s) in brown fat capable of stimulating Ucp1 expression.

Figure 3A:
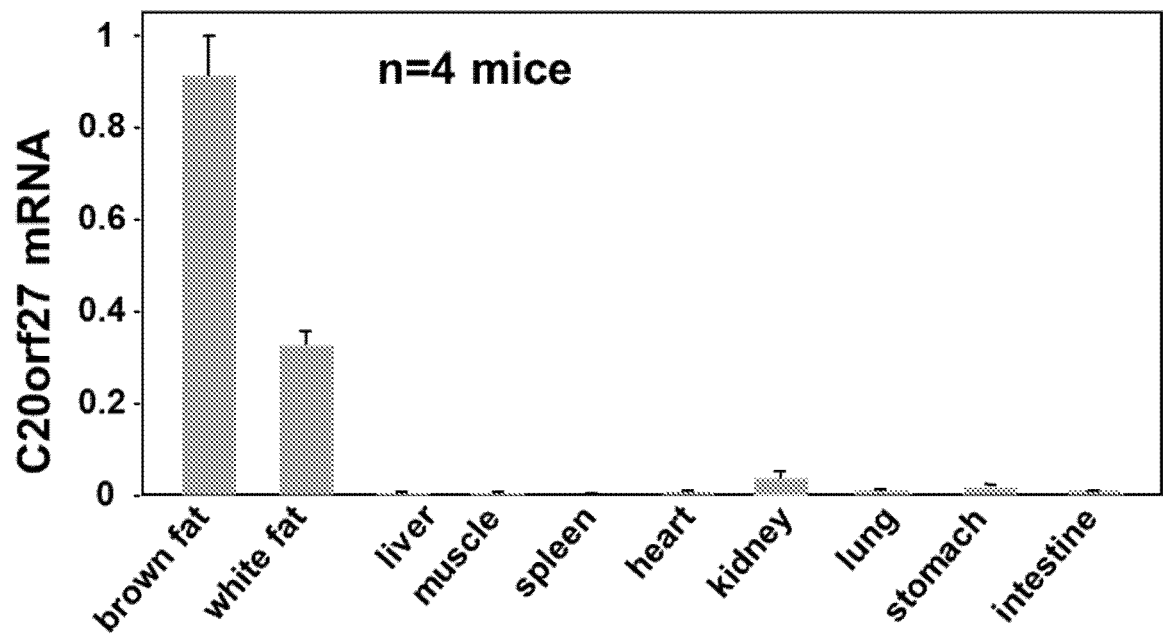
FIG. 3A. Tissue distribution of C20orf27 in mice (n=4 mice).
Figure 3B:
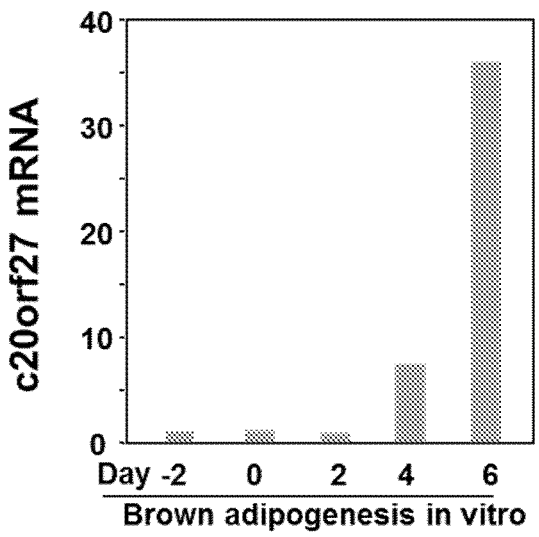
FIGS. 3B-3C. C20orf27 is expressed in mature adipocytes differentiated in vitro (3B) and in vivo (3C).
Figure 3C:
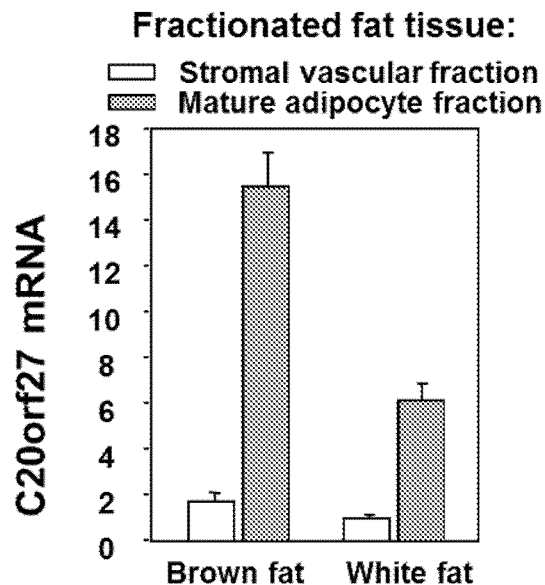

Example 2. Identification of C20orf27 as a Brown Fat-Selectively Expressed Adipokine We set out to identify the brown-fat promoting factors in the conditioned media. First, mouse brown adipocytes were differentiated in culture, and media conditioned by exposure to the brown adipocytes was collected and concentrated. The total proteins secreted into the conditional media from brown adipocytes were subjected to proteomic analysis by LC-MS/MS. Next, the identified proteins were analyzed in our published RNA-Seq datasets of mouse brown fat, white fat, and skeletal muscle (Pan et al., Developmental cell 35, 568-583 (2015)) to select for genes that are highly expressed in brown fat versus white fat and skeletal muscle. We then used a bioinformatic tool (Bendtsen et al., Protein Eng. Des. Sel. 17, 349-356 (2004)) to predict whether they are potentially secreted proteins. These combined analyses led to the identification of a previously uncharacterized gene C20orf27 that encodes a 19 kD protein with 174 amino acids. C20orf27 is highly conserved between mouse and human, and five unique peptides were identified in our proteomic analysis of conditional media (FIG. 2 and Table 4). Its transcript is abundantly present in brown fat (249 FPKM) that is 5-fold and 60-fold higher compared with white fat and skeletal muscle, respectively. C20orf27 was predicted by a bioinformatics tool (see Bendtsen et al., Protein Eng. Des. Sel. 17, 349-356 (2004)) to be a non-classically secreted protein with a high score (NN-score 0.804). RT-qPCR confirmed brown fat enrichment of C20orf27 and also showed extremely low expression of C20orf27 in other mouse tissues examined including liver, heart, skeletal muscle, kidney, lung, spleen, intestine, and stomach (FIG. 3A). C20orf27 was expressed in mature adipocytes with little expression in preadipocytes, as shown by both brown cell differentiation in vitro (FIG. 3B) and fractionated adipose tissue (FIG. 3C). These data together suggest that C20orf27 is a bona fide adipokine that is specifically expressed in adipose tissue and highly enriched in brown fat.

Figure 3D:
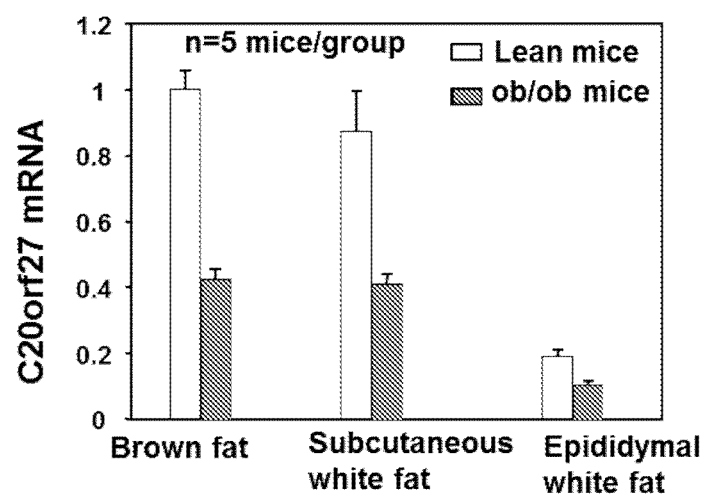
FIG. 3D. C20orf27 expression was decreased in obese (ob/ob) mice (n=5 mice/group).

Interestingly, C20orf27 expression was decreased in obese (ob/ob) mice (FIG. 3D).

TABLE 4

| Five unique peptides identified in C20orf27 | |
|---|---|
| Peptide sequence | SEQ ID NO: |
| FAAGHDAEGSQSHVHFDEK | 4 |
| YEITFTLPPVR | 5 |
| ETPVHSLHLK | 6 |
| LLSVTPTSEGYSIK | 7 |
| HHGTPMLLDGVK | 8 |

Example 3. Induction of C20orf27 Expression by Stimuli of White Fat Browning

Both cold exposure and exposure to β3-adrenergic receptor agonists have been shown to lead to browning of white fat. Acute cold exposure of mice at 4° C. for 6 hr induced C20orf27 expression (FIG. 4A) as well as Ucp1 expression in subcutaneous inguinal white fat, as did exposure to a single dose of β3-adrenergic receptor agonist CL316,243 (FIG. 4B). Rapid induction of C20orf27 by cold and by β3-adrenergic receptor agonist CL316,243 is consistent with a potential role of C20orf27 in brown fat development and browning of white fat.

Example 4. Confirm that C20orf27 is a Secreted Protein

Cultured brown adipocytes were infected with adenovirus expressing vector or C20orf27. Cell extract and medium were collected and protein detected using Western blot. Both endogenous and overexpressed C20orf27 protein was secreted into culture media (FIG. 5A). From several independent experiments based on equivalent loading, we estimated that at least 50% of C20orf27 protein is secreted into media. In the media fraction, but not in the cell extract fraction, we also observed a lower band of C20orf27; it remains to be determined whether this band is a product of active processing or a degradation product in the media.

The CRISPR-Cas9 system was also used to knock in a Flag tag at the C-terminus of genomic locus of C20orf27 in brown adipocytes. Flag antibody detected Flag tagged C20orf27 in the culture media as shown in FIG. 5B.

Figure 5C:
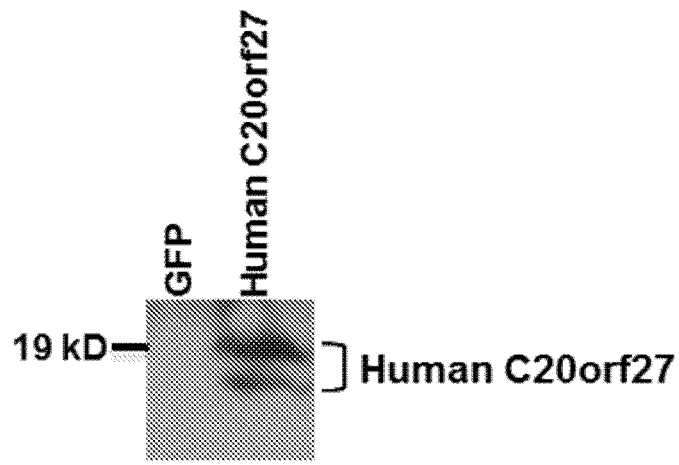
FIG. 5C. Detection of C20orf27 in circulation of mice that expressed human C20orf27 in liver.

Finally, human C20orf27 was expressed in mouse liver through adenovirus tail vein injection. One week after injection, blood samples were taken and processed for western blot analysis. We found human C20orf27 could be easily detected in the blood (FIG. 5C). These results confirm that C20orf27 is indeed a secreted protein in vivo that may act in an endocrine manner.

Example 5. C20orf27 is Essential for Brown Adipocyte Differentiation In Vitro Using lentiviral shRNA (target sequence GACAACAGCTTCTTAGTCA (SEQ ID NO:9)) delivery, we were able to knockdown C20orf27 by more than 90%. In vitro differentiation into brown adipocytes was completely blocked in the C20orf27 knockdown brown preadipocytes, whereas brown preadipocytes infected with a control virus displayed a 100% differentiation. These data indicate that C20orf27 might control brown fat development in an autocrine and/or paracrine manner.

This impaired brown adipogenesis was rescued by conditioned medium containing C20orf27. We overexpressed C20orf27 in HEK293 cells and collected conditioned medium. When the conditioned medium was applied to the C20orf27 knockdown brown preadipocytes, adipogenesis was partially rescued, whereas conditioned medium collected from vector control HEK293 cells had no effect. These results support the idea that secreted C20orf27 that was exogenously expressed in HEK293 cells is functional.

Figures 6A, 6B, 6C:
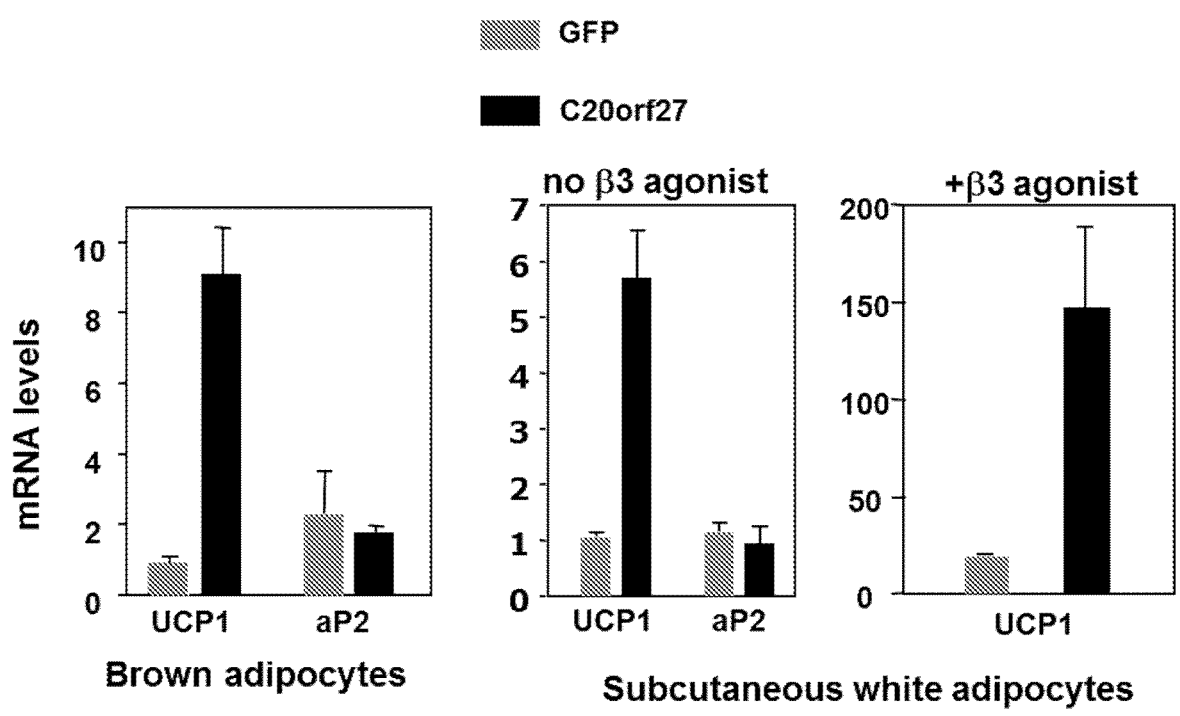
FIGS. 6A-6C. (6A) Gene expression in differentiated brown adipocytes infected with adenoviruses overexpressing C20orf27. (6B-6C) Gene expression in differentiated primary white adipocytes infected with adenoviruses over-expressing C20orf27 in the absence (6B) and presence (6C) of β-adrenergic receptor agonist CL316,243.

Example 6. Exogenous C20orf27 Promotes UCP-1 Expression in Brown and White Adipocytes We prepared adenoviruses expressing C20orf27. Immortalized brown preadipocytes were differentiated and infected with the viruses at late stage of differentiation. We infected the adipocytes at their late stage of differentiation to potentially minimize the effect of C20orf27 on adipogenesis per se, thereby testing whether C20orf27 has a direct role in Ucp1 expression. Visualization of adipocyte lipid droplet found no difference between C20orf27-infected and GFP infected brown adipocytes. On the other hand, overexpression of C20orf27 robustly promoted the expression of brown fat marker Ucp1 compared with control viruses, whereas expression of the general fat marker aP2 remained unchanged (FIG. 6A). Similarly, we overexpressed C20orf27 in primary inguinal white fat adipocytes at their late stage of differentiation, and found that Ucp1 was strongly induced (FIG. 6B). Addition of β3-adrenergic receptor agonist typically increased Ucp1 expression by more 20 to 30-fold; induction of Ucp1 by C20orf27 overexpression also occurred in the presence of β3-adrenergic receptor agonist (FIG. 6C), indicating an additive or synergistic effect. These results suggest a direct role of C20orf27 in Ucp1 expression independent of differentiation.

Figure 7:
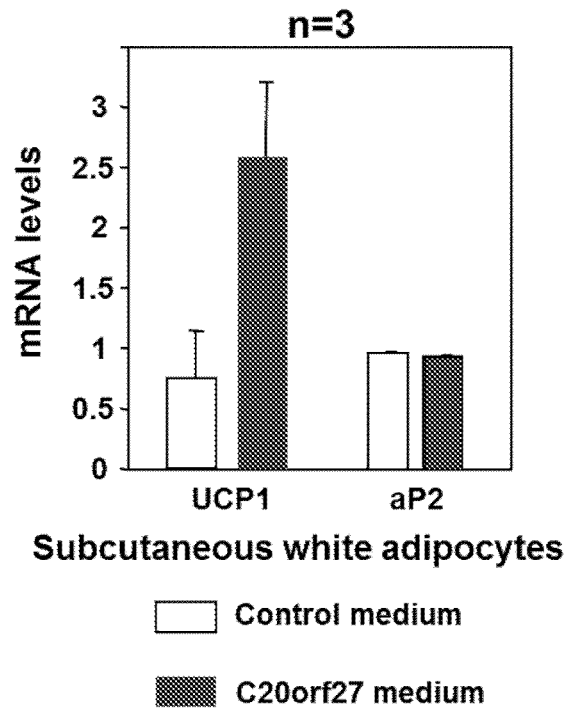
FIG. 7. Gene expression in differentiated primary white adipocytes treated with conditional medium containing C20orf27 protein.

In addition, conditioned medium containing C20orf27 stimulated Ucp1 expression in white adipocytes. We added conditioned medium collected from C20orf27 overexpressing HEK293 cells to differentiated inguinal white adipocytes for 16 hr, and found that Ucp1 expression was induced compared to conditional medium collected from vector control cells (FIG. 7). Importantly, this short-term treatment had no effect on adipogenesis per se or on expression of common adipocyte markers. The data suggest a potentially important role of C20orf27 in conversion of white adipocytes to brown-like adipocytes.

Example 7. Fat-Specific C20orf27 Transgenic Mice and Knockout Mice

Figure 8A:
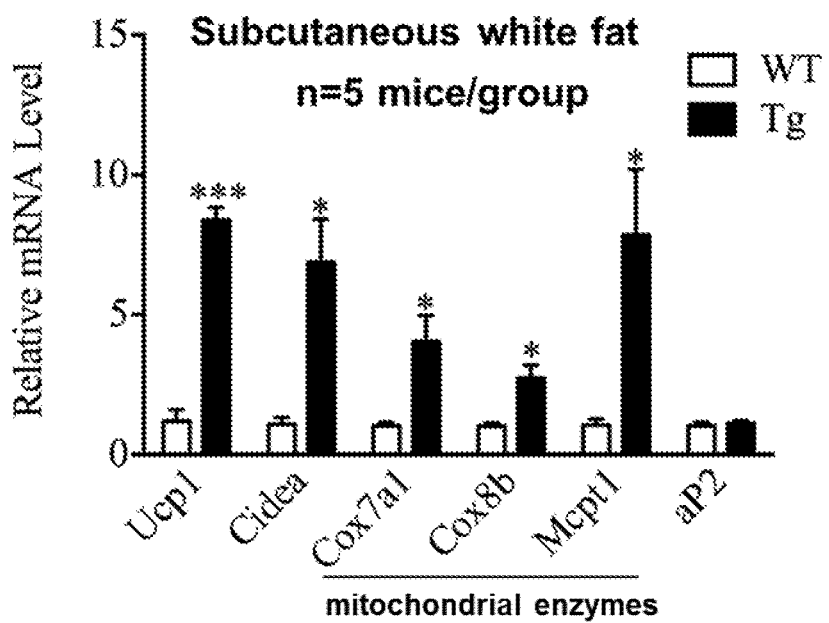
Figure 8B:
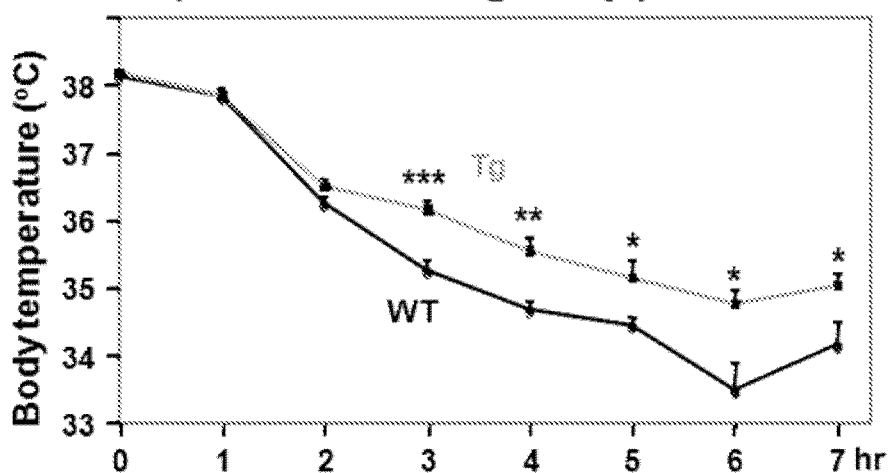
Figure 8C:
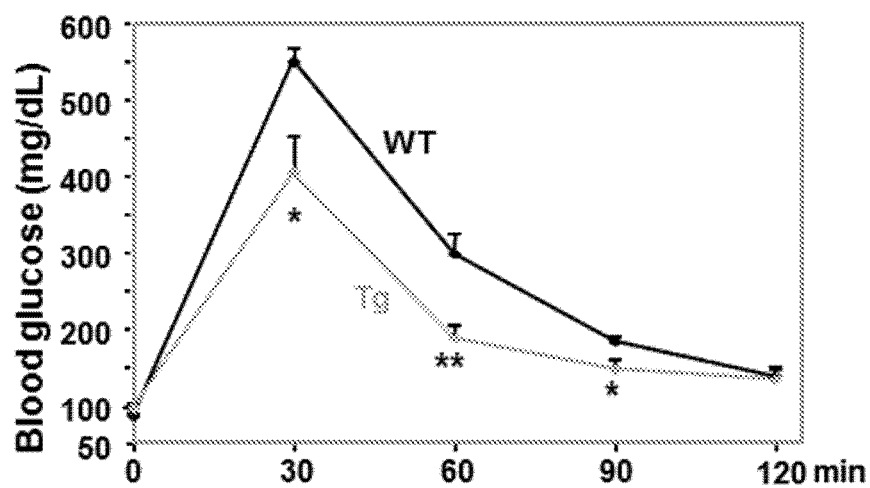

To understand the chronic, autocrine/paracrine effect of C20orf27 in adipose tissue, we generated transgenic mice to overexpress C20orf27 in adipose tissue. C20orf27 cDNA was fused downstream of the 5.4-kb aP2 promoter, a promoter that directs adipose tissue-selective gene expression. Transgenic mouse lines were generated by injection of the C20orf27 transgene into fertilized mouse embryos. On normal chow diet, the transgenic mice had similar food consumption and body weights as control mice, but white adipocytes were smaller, and expressed higher levels of UCP1 and mitochondrial enzymes (FIG. 8A). Ucp1 immunostaining further confirmed a robust browning of white fat. Importantly, the mice were more cold-tolerant, indicating that browned white fat have increased energy expenditure (FIG. 8B). They also had improved glucose tolerance compared with wild type littermates (FIG. 8C).

Figure 8D:
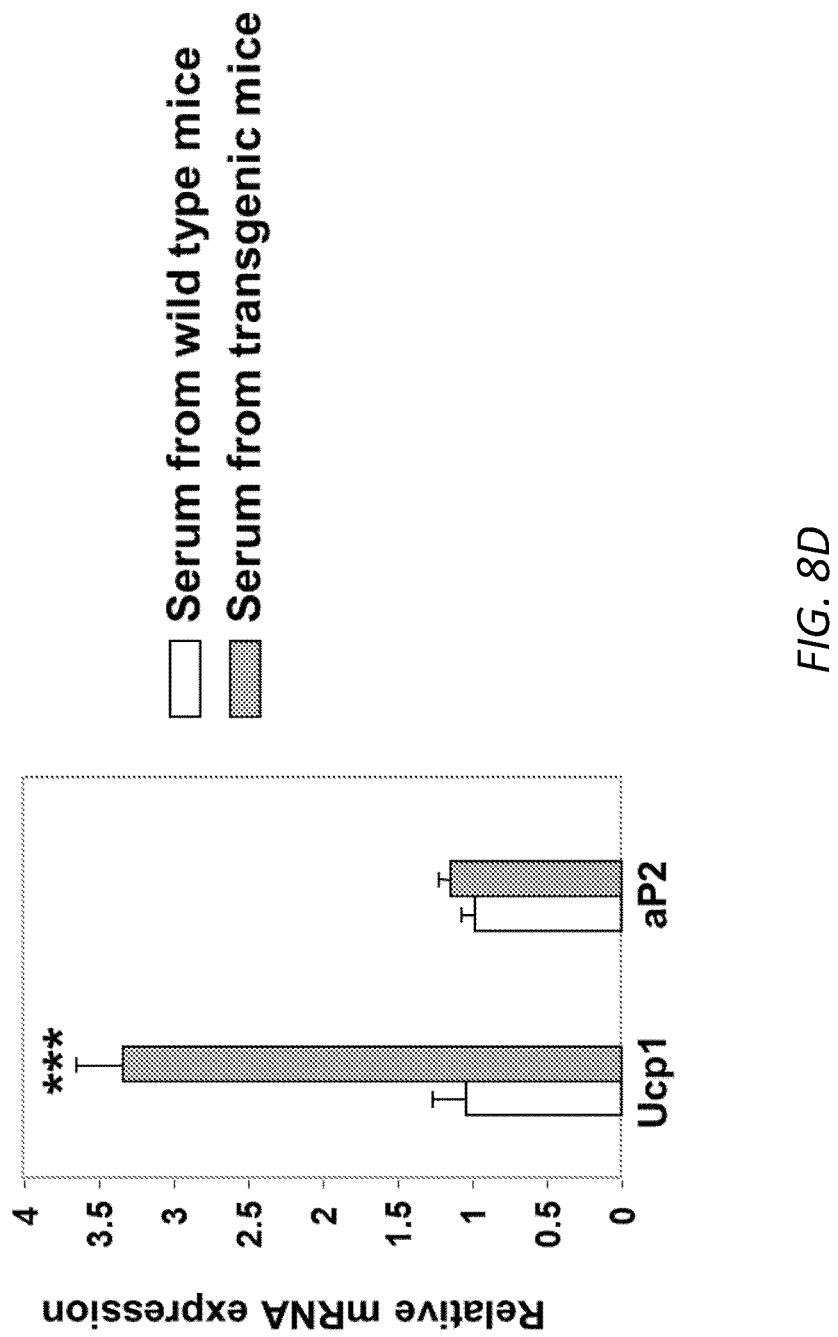

To functionally assess the presence of C20orf27 protein in circulation, mouse serum was collected, and added into the culture media of primary white adipocyte culture. Serum from transgenic mice induces Ucp1 expression compared with serum from control littermates (FIG. 8D). These data are consistent with the idea that C20orf27 is indeed secreted and remains active.

Figure 8F:
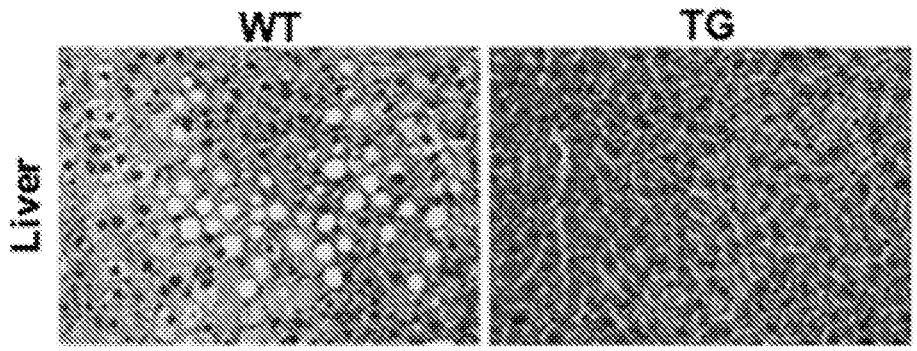

To determine whether the browned white fat in the transgenic mice is able to counteract obesity, we fed the mice with a high fat diet. The C20orf27 transgenic mice gained significantly less body weight than control littermates (FIG. 8E) and had decreased lipid accumulation in the livers (FIG. 8F).

Figure 9A:
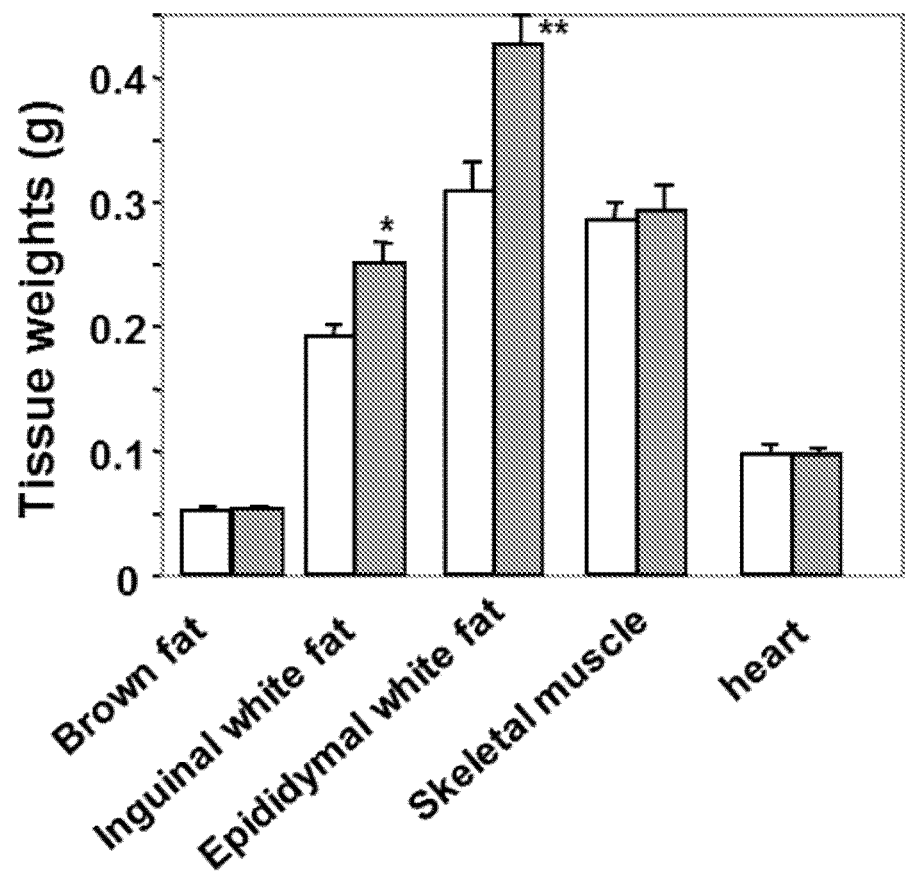
FIG. 9A. Adipose tissue-specific C20orf27 knockout (FKO) mice had increased white fat mass. n=4-6 three-month-old male mice/group with a normal chow diet. White bar, control f/f mice; grey bar; FKO mice.

In contrast, adipose tissue-specific C20orf27 knockout (FKO) mice had increased white fat mass, as shown in FIG. 9A. Furthermore, histology analysis showed that adipocytes in the FKO mice were larger in size, and immunostaining and western blot analyses revealed that these adipocytes expressed less Ucp1 compared with adipocytes from control mice, suggesting decreased white browning. Thus, the phenotypes of FKO mice are the opposite of those of C20orf27 transgenic mice.

Figure 9B:
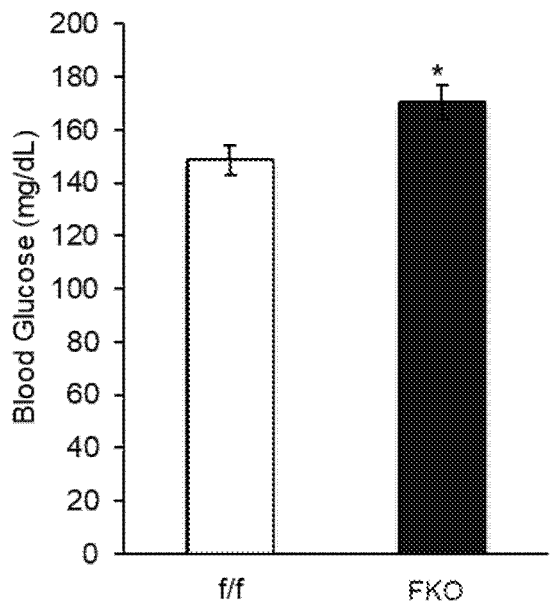
FIG. 9B. Blood glucose was measured in control (f/f) and fat-specific C20orf27 knockout (FKO) mice after a 5-hour fasting. n=8 mice/group, *p<0.05.
Figure 10A:
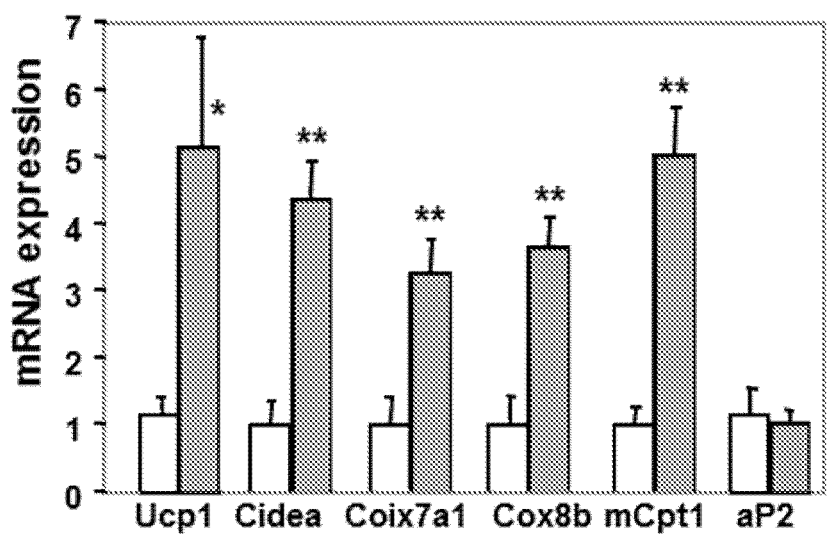
FIGS. 10A-10B. Hepatic expression of mouse (10A) or human (10B) C20orf27 through adenovirus induced Ucp1 and mitochondrial gene expression in subcutaneous white fat. White Bar, GFP, blue Bar, C20orf27. n=5 mice/group.
Figure 10B:
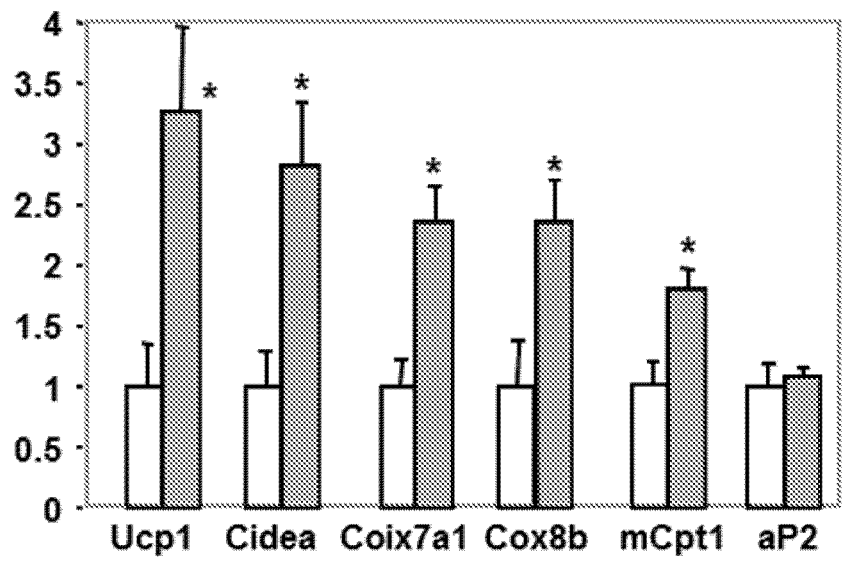
Figure 10C:
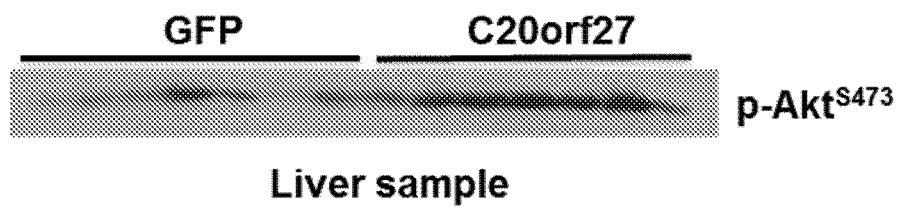
FIG. 10C. Hepatic expression of adenoviral expression of mouse C20orf27 in the liver increased Akt phosphorylation.
Figure 10D:
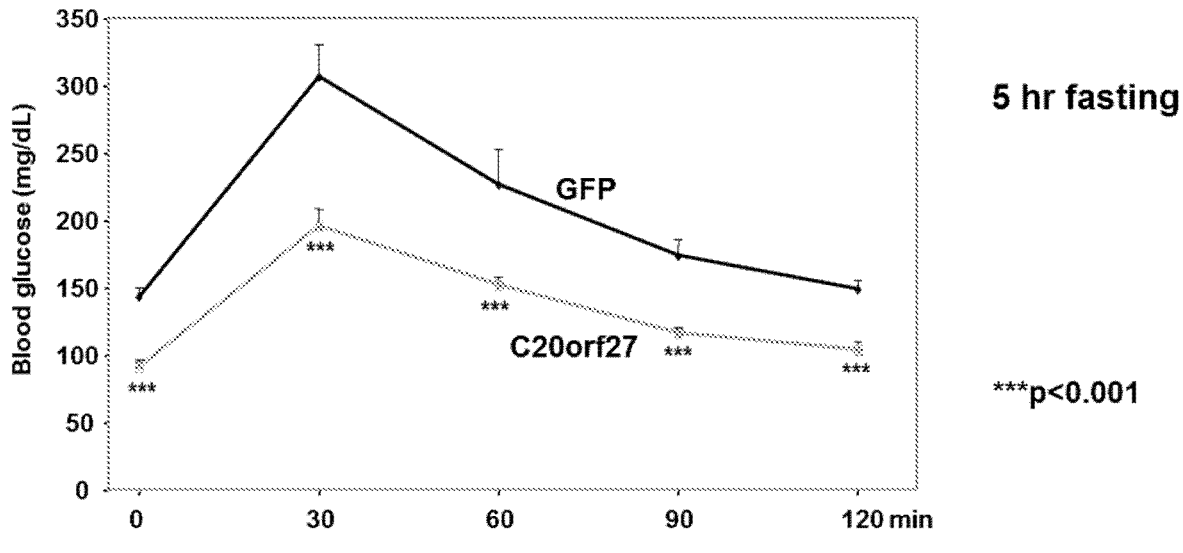
FIGS. 10D-10E. Hepatic expression of mouse (10D, n=9) or human (10E, n=6) C20orf27 through adenovirus lowered basal glucose level and improved glucose tolerance.
Figure 10E:
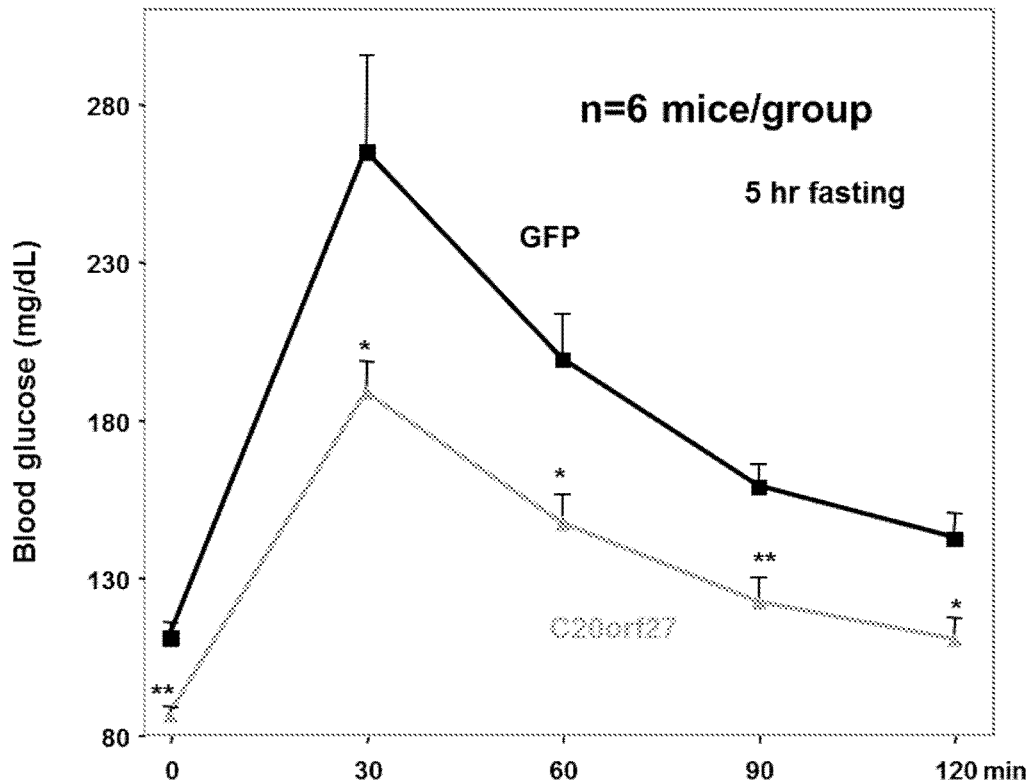

To evaluate the effects of C20orf27 knockout on basal blood glucose level, FKO and control mice (n=8 mice/group) were fed a normal chow diet. Blood glucose was measured in 5-month-old female control (f/f) and FKO mice after a 5-hour fasting. The results, shown in FIG. 9B,

Example 8. Exogenous C20orf27 Promotes White Fat Browning and Improves Glucose Homeostasis In Vivo We cloned C20orf27 cDNA into an adenoviral vector, driven by a CMV promoter. We prepared adenoviruses and injected them into wild type mice (n=5/group) through tail vein. This tail vein delivery allows adenoviruses to be selectively uptaken by the liver, thus C20orf27 protein would be ectopically expressed in the liver. One week after injection, gene expression in adipose tissue was measured. As shown in FIGS. 10A-10B, compared with GFP control, hepatic expression of either mouse or human C20orf27 though adenovirus induced Ucp1 and mitochondrial gene expression in subcutaneous white fat. The data suggest that C20orf27 is a hormone that can act in an endocrine manner to promote browning of white fat. In addition, liver Akt phosphorylation was measured. The results, shown in FIG. 10C, indicated that adenoviral expression of C20orf27 in the liver increased Akt phosphorylation. To determine the effect of C20orf27 on glucose homeostasis, wild type mice (n=6-9/group) were infused with adenovirus to express mouse or human C20orf27 in the liver. Glucose tolerance tests were performed in these mice, and a significant improvement of both basal glucose level and glucose tolerance was observed as shown in FIGS. 10D-E; similar effects were observed after we tail vein injected C20orf27 adenovirus into obese mice induced by a high fat-diet. These results suggest an important role of C20orf27 in glycemic control.

Figure 11:
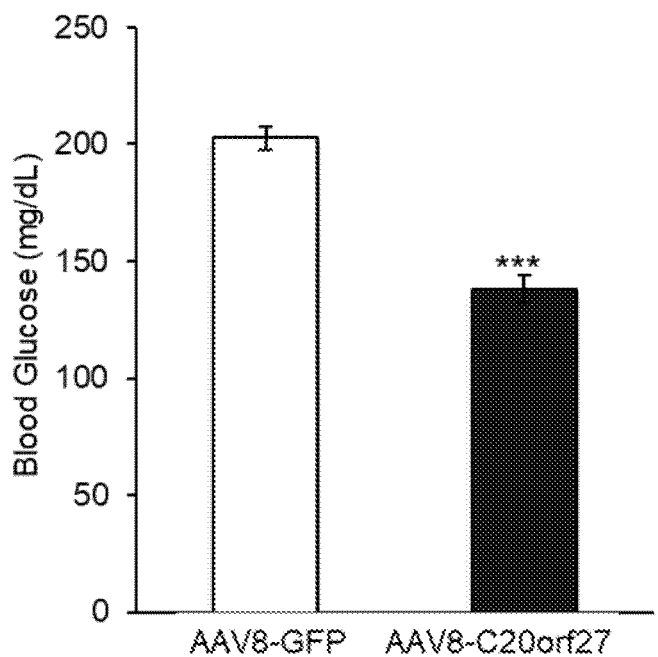
FIG. 11. Wild type mice were tail vein-injected with AAV8 viruses expressing either GFP or human C20orf27, and then fed a high fat diet. Four weeks after high fat feeding, blood glucose levels were measured after a 5-hour fasting. n=9 mice/group, ***p<0.001.

In addition, AAV8-GFP and AAV8-human C20orf27 viruses driven by the human thyroid hormone-binding globulin promoter, which allows liver-specific gene expression, were produced. 8-week-old wild type male mice were tail vein-injected with viruses at 3×10^11 genomic copies/mouse (n=9 mice/group), and were then shifted to a high fat diet. Four weeks after high fat feeding, blood glucose levels were measured after a 5-hour fasting. The results, shown in FIG. 11, demonstrated that hepatic expression of human C20orf27 through adeno-associated virus (AAV) prevented high fat diet-induced hyperglycemia.

Example 9. C20orf27 Activates Protein Kinase A in Adipocytes

Figure 12A:
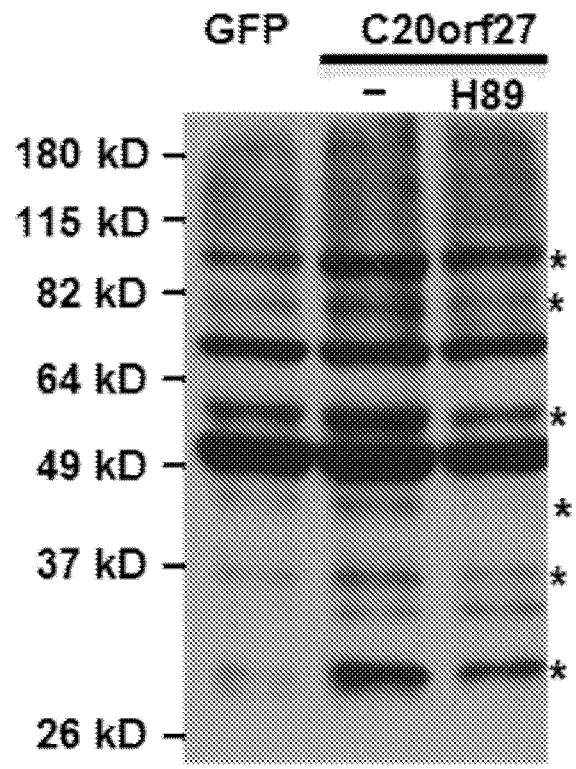
FIGS. 12A-12B. Mouse (12A) and human (12B) C20orf27 expression in adipocytes increased phosphorylation of PKA substrates, which was decreased by PKA inhibitor H89.
Figure 12B:
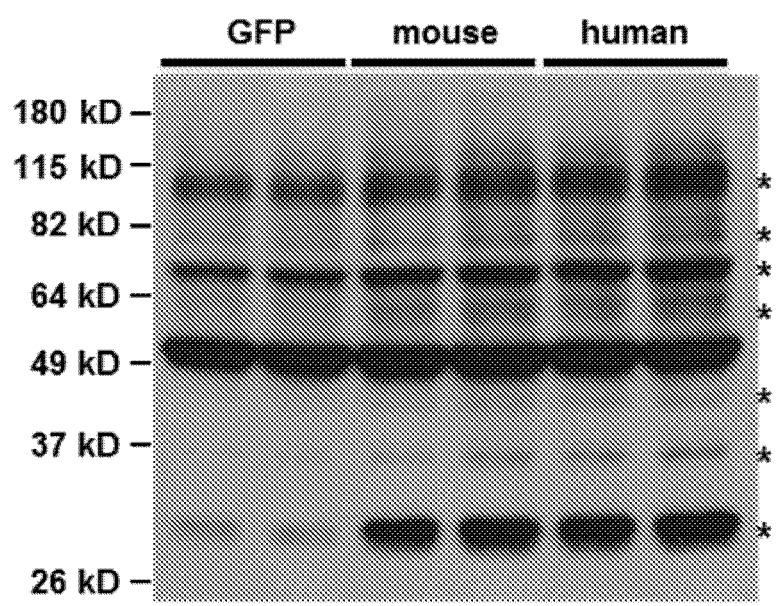

The PKA pathway is a central pathway for promoting thermogenesis and white fat browning (Lowell and Spiegelman, Nature 404, 652-660 (2000)). To determine whether C20orf27 is acting through PKA, primary inguinal white fat adipocytes were infected with adenovirus expressing C20orf27 or GFP. Cells were then treated with or without PKA inhibitor H89 (30 μM) for 3 hr before harvesting for western blot analysis with a antibody against phospho-PKA substrates. As shown in FIGS. 12A-12B, mouse and human C20orf27 expression, respectively, increased phosphorylation of PKA substrates, which was decreased by PKA inhibitor H89.

To determine where C20orf27 was acting, C20orf27 was fused to the C-terminus of Secreted Placental Alkaline Phosphatase (SEAP) and then expressed in HEK293 cells. SEAP alone was used as a control. The conditioned media was collected and concentrated, the incubated with frozen adipose slices. The slices were washed and SEAP activity assayed to detect the interaction between C20orf27 and cell surface. The results showed SEAP activity in brown fat and subcutaneous white fat. Thus, C20orf27 appears to bind to putative receptor(s) in brown fat, and subcutaneous white fat. These results suggest a potential mechanism, that is, C20orf27 binds to its receptor on adipocyte cell surface to activate PKA pathway, which subsequently leads to white fat browning.

REFERENCES

1. Rosen, E. D. & Spiegelman, B. M. What we talk about when we talk about fat. Cell 156, 20-44 (2014).
2. Cypess, A. M., et al. Identification and importance of brown adipose tissue in adult humans. N Engl J Med 360, 1509-1517 (2009).
3. Cypess, A. M., et al. Anatomical localization, gene expression profiling and functional characterization of adult human neck brown fat. Nat Med 19, 635-639 (2013).
4. Jespersen, N. Z., et al. A classical brown adipose tissue mRNA signature partly overlaps with brite in the supraclavicular region of adult humans. Cell Metab 17, 798-805 (2013).
5. Lidell, M. E., et al. Evidence for two types of brown adipose tissue in humans. Nat Med 19, 631-634 (2013).
6. Nedergaard, J., Bengtsson, T. & Cannon, B. Unexpected evidence for active brown adipose tissue in adult humans. Am J Physiol Endocrinol Metab 293, E444-452 (2007).
7. van Marken Lichtenbelt, W. D., et al. Cold-activated brown adipose tissue in healthy men. N Engl J Med 360, 1500-1508 (2009).
8. Virtanen, K. A., et al. Functional brown adipose tissue in healthy adults. N Engl J Med 360, 1518-1525 (2009).
9. Zingaretti, M. C., et al. The presence of UCP1 demonstrates that metabolically active adipose tissue in the neck of adult humans truly represents brown adipose tissue. FASEB journal: official publication of the Federation of American Societies for Experimental Biology 23, 3113-3120 (2009).
10. Wu, J., et al. Beige adipocytes are a distinct type of thermogenic fat cell in mouse and human. Cell 150, 366-376 (2012).
11. Saito, M., et al. High incidence of metabolically active brown adipose tissue in healthy adult humans: effects of cold exposure and adiposity. Diabetes 58, 1526-1531 (2009).
12. Cristancho, A. G. & Lazar, M. A. Forming functional fat: a growing understanding of adipocyte differentiation. Nat Rev Mol Cell Biol 12, 722-734 (2011).
13. Rosen, E. D. & MacDougald, O. A. Adipocyte differentiation from the inside out. Nat Rev Mol Cell Biol 7, 885-896 (2006).
14. Farmer, S. R. Transcriptional control of adipocyte formation. Cell metabolism 4, 263-273 (2006).
15. Tontonoz, P. & Spiegelman, B. M. Fat and beyond: the diverse biology of PPARgamma. Annu Rev Biochem 77, 289-312 (2008).
16. Harms, M. & Seale, P. Brown and beige fat: development, function and therapeutic potential. Nature medicine 19, 1252-1263 (2013).
17. Kajimura, S., Seale, P. & Spiegelman, B. M. Transcriptional control of brown fat development. Cell metabolism 11, 257-262 (2010).
18. Puigserver, P., et al. A cold-inducible coactivator of nuclear receptors linked to adaptive thermogenesis. Cell 92, 829-839 (1998).

19. Seale, P., et al. Transcriptional control of brown fat determination by PRDM16. Cell metabolism 6, 38-54 (2007).
20. Farmer, S. R. Molecular determinants of brown adipocyte formation and function. Genes Dev 22, 1269-1275 (2008).
21. Uldry, M., et al. Complementary action of the PGC-1 coactivators in mitochondrial biogenesis and brown fat differentiation. Cell Metab 3, 333-341 (2006).
22. Wang, G. X., et al. The brown fat-enriched secreted factor Nrg4 preserves metabolic homeostasis through attenuation of hepatic lipogenesis. Nature medicine (2014).
23. Bostrom, P., et al. A PGC1-alpha-dependent myokine that drives brown-fat-like development of white fat and thermogenesis. Nature 481, 463-468 (2012).
24. Kharitonenkov, A., et al. FGF-21 as a novel metabolic regulator. The Journal of clinical investigation 115, 1627-1635 (2005).
25. Inagaki, T., et al. Endocrine regulation of the fasting response by PPARalpha-mediated induction of fibroblast growth factor 21. Cell metabolism 5, 415-425 (2007).
26. Badman, M. K., et al. Hepatic fibroblast growth factor 21 is regulated to by PPARalpha and is a key mediator of hepatic lipid metabolism in ketotic states. Cell metabolism 5, 426-437 (2007).
27. Pan, D., Fujimoto, M., Lopes, A. & Wang, Y. X. Twist-1 is a PPARdelta-inducible, negative-feedback regulator of PGC-1alpha in brown fat metabolism. Cell 137, 73-86 (2009).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating, or reducing risk of, obesity or a disorder associated with obesity, or a method of improving glycemic control, in a mammalian subject, wherein the method comprises administering a therapeutically effective amount of Chromosome 20 Open Reading Frame 27 (C20orf27) polypeptide to a subject in need thereof, wherein the disorder associated with obesity is diabetes, metabolic syndrome, fatty liver disease, or non-hepatic steatosis.

2. The method of claim 1, wherein the polypeptide comprises the amino acid sequence of SEQ ID NO:2.

3. The method of claim 1, wherein the subject has a body mass index (BMI) of at least 25.

4. The method of claim 1, wherein the subject is human.

5. The method of claim 1, wherein the polypeptide is administered parenterally.

6. The method of claim 5, wherein the polypeptide is administered intravenously, intramuscularly, or subcutaneously.

7. The method of claim 1, wherein the polypeptide comprises one or more modifications selected from the group consisting of:
    replacement of one or more L amino acids with D amino acids; acetylation; amidation;
    conjugation to a linear or branched-chain monomethoxy poly-ethylene glycol (PEG);
    modification of the N- or C-terminus; and glycosylation.

8. The method of claim 1, wherein the polypeptide is fused to a non-C20orf27 protein selected from the group consisting of immunoglobin Fc, human serum albumin, transferrin, and carboxy-terminal peptide of chorionic gonadotropin (CG) β-chain.

* * * * *